United States Patent [19]

Yamauchi

[11] Patent Number: 5,639,623
[45] Date of Patent: Jun. 17, 1997

[54] METHOD OF MEASURING IMMUNOKINETICS

[76] Inventor: Tamio Yamauchi, 2-2-29, Hazawa, Nerima-ku, Tokyo, 176, Japan

[21] Appl. No.: 181,867

[22] Filed: Jan. 13, 1994

Related U.S. Application Data

[63] Continuation of Ser. No. 689,054, filed as PCT/JP90/01148, Sep. 7, 1990, abandoned.

[30] Foreign Application Priority Data

Sep. 8, 1989 [JP] Japan .................................. 1-234484

[51] Int. Cl.$^6$ ............................................. G01N 33/53
[52] U.S. Cl. ........................................................ 435/7.24
[58] Field of Search ........................................ 435/7.24

[56] References Cited

FOREIGN PATENT DOCUMENTS 71659  11/1987  Australia.
63-502695  9/1987  Japan.

OTHER PUBLICATIONS

Schuller et al 1986 Arch Otolaryngol Head Neck Surg 112: 938–941.
Wolfe et al 1987 Arch Otolaryngol Head Neck Surg 113: 1200–1206.
Catalona et al 1979 J Immunol 122(3): 1009–1014.
Sokal et al 1981 Biometry, 2nd Ed. W H Freeman & Company, Chapter 16.
Sokol & Rohef 1981. Biometry W. H Freeman & Company, San Francisco. Chapter 16.
Mae et al. 1991. Advanced Immunology Gorver Medical Publishing Company Yada, Chap. 1.
"Present Status of Cellular Immunity Inspection", Inspection and Technology, extra edition, Jun., 1988.
"Immunologic Determinants of Head and Neck Cancer Response to Induction Chemotherapy", S. Schantz; J. Clin. Oncol., 1989.
"Methionine–Enkephalin as Immunomodulator Therapy in Human Immunodeficiency Virus Infections: Clinical and Immunological Effects", K. Zunich et al.; J. Clin. Immunol., 1988.
Zunich et al, Journal of Clinical Immun., vol. 8, No. 2, pp. 95–102 (1988).
Schantz et al, Journal of Clinical Oncol., vol. 7, No. 9 pp. 857–864 (1989).
Inspection & Technology, extra. ed., Immunochemical Inspection Method, vol. 16, No. 7 (1988).
Kumagai et al, Biological Abstracts, vol. 81, No. 3, Abstract No. 25264, p. 643 (1986).
Kohno et al, extra ed., Immunochemical Inspection Method, vol. 16, No. 7, pp. 902–904 (1988).
Japanese Patent Appln. No. JP, A, 63–502695.

*Primary Examiner*—Vasu S. Jagannathan
*Assistant Examiner*—Karen Cochrane Carlson
*Attorney, Agent, or Firm*—Birch, Stewart, Kolasch & Burch, LLP

[57] ABSTRACT

A method of measuring and assessing T and B cell immunokinetics in human, particularly cancer immunokinetics by applying the multiple regression analysis, one of multivariate data analyses, to the counts in blood samples of CD3, CD4, CD8 and OKIa1 positive lymphocytes, helper, suppression inducer, cytotoxic and suppressor T lymphocytes, activated suppression inducer/helper and activated suppressor/cytotoxic T lymphocytes and natural killer cell, monocyte, basophil, eosinophil and neutrophil.

20 Claims, 12 Drawing Sheets

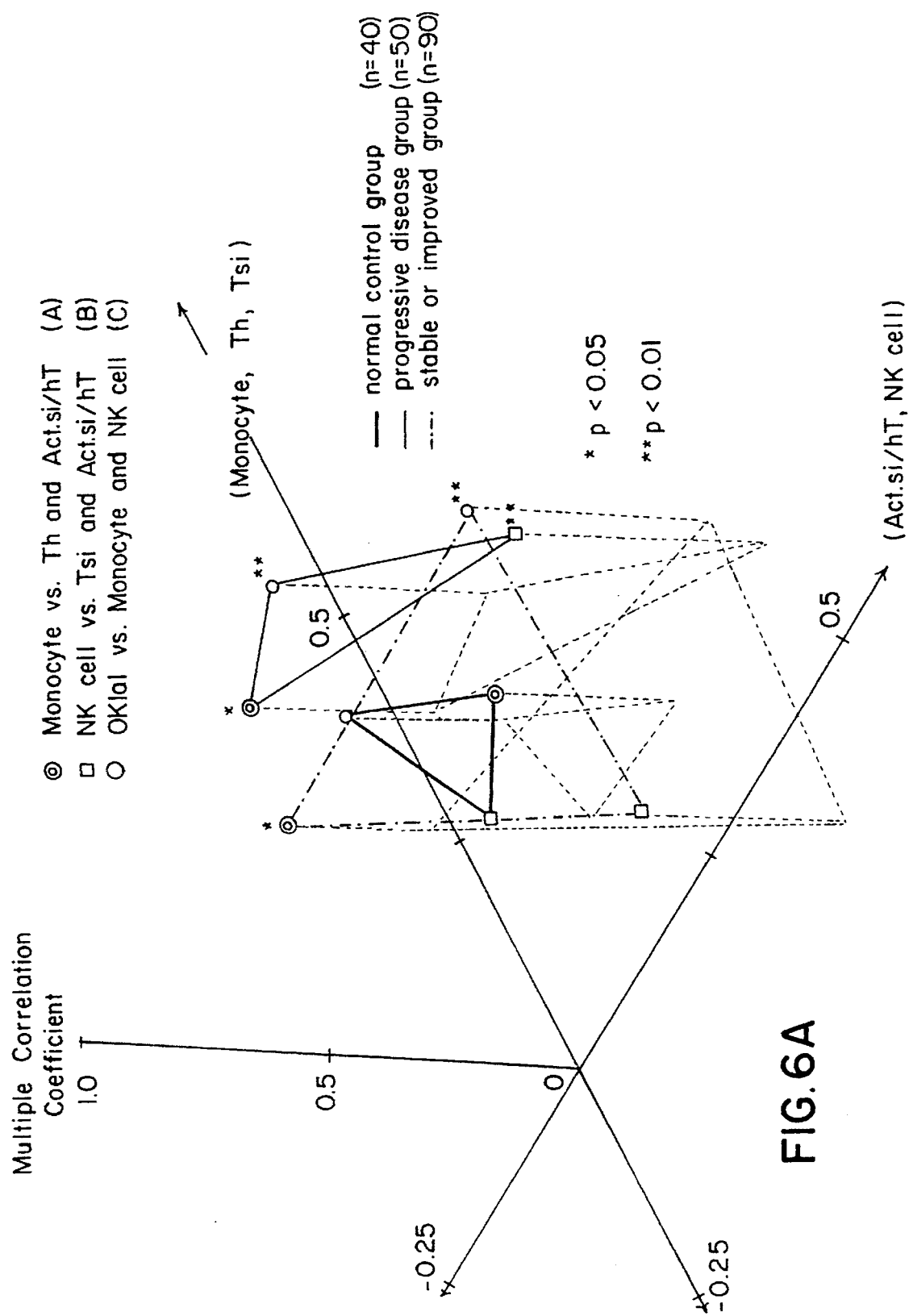

- △ Monocyte vs. Th and Act.si/hT (A)
- □ NK cell vs. Tsi and Act.si/hT (B)
- • OKIa1 vs. Monocyte and Act.si/hT (C)
- ○ Activated T Lymphocyte vs. Monocyte and NK cell (D)
- ⊚ Activated B Lymphocyte vs. Monocyte and NK cell (E)

\* $p < 0.05$ (f-test)
\*\* $p < 0.01$ progressive disease group
(n=50)

| | | |
|---|---|---|
| △ | Monocyte vs. Th and Act.si/hT | (A) |
| □ | NK cell vs. Tsi and Act.si/hT | (B) |
| ● | OKIa1 vs. Monocyte and Act.si/hT | (C) |
| ○ | Activated T Lymphocyte vs. Monocyte and NK cell | (D) |
| ⊚ | Activated B Lymphocyte vs. Monocyte and NK cell | (E) |

\* $p < 0.05$ (f-test)

\*\* $p < 0.01$ stable or improved group
(n=93)

△ Monocyte vs. Th and Act.si/hT (A)
□ NK cell vs. Tsi and Act.si/hT (B)
● OKIa1 vs. Monocyte and Act.si/hT (C)
○ Activated T Lymphocyte vs. Monocyte and NK cell (D)
⊚ Activated B Lymphocyte vs. Monocyte and NK cell (E)

\* p 0.05 (f-test)
\*\*p 0.01

METHOD OF MEASURING IMMUNOKINETICS

This application is a continuation, of application Ser. No. 07/689,054 filed as PCT/JP90/01148 Sep. 7, 1990, now abandoned.

FIELD OF INDUSTRIAL APPLICATION

This invention is a method of measuring cellular immunokinetics based upon the recognition mechanism of various antigens in human beings.

BACKGROUND OF INVENTION

With the recent development of technology in anticancer immunotherapy, a wide variety of remedies have been developed and various therapeutic methods devised. However, the cellular immunity in relation to immunotherapy in humans has not yet been completely elucidated.

The inventor has made analysis and comparison to examine how effective and ineffective cases differ or what the immune state in normal healthy persons without past histories of malignant neoplasms like cancers or sarcomas is like, taking, as examples, patients with metastatic renal cancer who had undergone an aggressive interferon-alpha ($\alpha$-IFN) treatment to continuously monitor the kinetics of activated suppression inducer/helper, helper and suppression inducer T lymphocytes, NK cell, OKIa1 positive lymphocyte and so on.

As a result, it has been found that by the multiple regression analysis (MRA), which is one of multivariate data analyses, for the correlation of monocyte with helper and activated suppression inducer/helper T lymphocytes, new and important findings in respect of cellular immunity, especially cancer immunokinetics, are obtained.

More specifically, it has now been found that the above-mentioned analysis renders it possible to estimate the function of autologous tumor antigen recognition mechanism (ATARM), the possibility of progress from carcinogenesis to nosogenesis and the presence, state and details of malignant neoplasm and is accordingly useful for the detection of cancers, tumors etc. and can be utilized as indices for the efficacy of their treatments.

As for activated suppression inducer/helper, helper and suppression inducer T lymphocytes, NK cell and OKIa1 positive lymphocyte, these lymphocytes have only been measured individually and the mutual relationships among them have never been examined to date. That is to say, it is the real state of things that the significance of the results of such measurement has never been made clear and that immunokinetics have never been grasped on the basis of such results.

The object of this invention is to provide a method of measuring immunokinetics, which permits immunokinetics of cellular immunity, especially cancer immunity, to be grasped in a straightforward manner, and further can serve as an index for the diagnosis, treatment, prognosis etc. of different diseases, in particular autoimmune diseases like bronchial asthma, atopic dermatitis etc. hereditary gene diseases causing abnormal immune states, immune from organ transplantation, viral diseases affecting cellular immunity like serum hepatitis, cancer etc.

DISCLOSURE OF INVENTION

The inventor has succeeded in the assessment of cellular immunokinetics, especially cancer immunokinetics, by the MRA, which is one of multivariate data analyses, of the counts in human blood samples of activated suppression inducer/helper, activated suppressor/cytotoxic, suppression inducer, helper, suppressor and cytotoxic T lymphocytes, CD3, CD4, CD8 and OKIa1 positive lymphocytes, monocyte and NK cell.

Accordingly, the gist of this invention consists of the following 1–9:

1. A method of measuring immunokinetics through blood analysis, characterized by carrying out the following process steps (a)–(f) to assess the antigen recognition mechanism:
   a) The counts of monocyte, helper T lymphocyte and activated suppression inducer/helper T lymphocyte in blood samples are measured;
   b) The multiple regression analysis using monocyte as dependent variable and helper and activated suppression inducer/helper T lymphocytes as independent variables is carried out;
   c) The respective partial regression coefficients of helper and activated suppression inducer/helper T lymphocytes are determined and the significances are tested;
   d) The multiple correlation coefficient is determined and the significance is tested;
   e) The contributions of helper and activated suppression inducer/helper T lymphocytes are determined; and
   f) The correlations between monocyte, helper T lymphocyte and activated suppression inducer/helper T lymphocyte are determined.

2. A method of measuring immunokinetics through blood analysis, characterized by carrying out the following process steps (a)–(f) to assess the suppressive function of NK cell on suppression inducer T lymphocytes:
   a) The counts of NK cell, suppression inducer T lymphocyte and activated suppression inducer/helper T lymphocyte in blood samples are measured;
   b) The multiple regression analysis using NK cell as dependent variable and suppression inducer and activated suppression inducer/helper T lymphocytes as independent variables is carried out;
   c) The respective partial regression coefficients of suppression inducer and activated suppression inducer/helper T lymphocytes are determined and the significances are tested;
   d) The multiple correlation coefficient is determined and the significance is tested;
   e) The contributions of suppression inducer and activated suppression inducer/helper T lymphocytes are determined; and
   f) The correlations between NK cell, suppression inducer and activated suppression inducer/helper T lymphocytes are determined.

3. A method of measuring immunokinetics through blood analysis, characterized by carrying out the following process steps (a)–(f) to assess the function of NK cell and monocyte against OKIa1 positive lymphocyte:
   a) The counts of OKIa1 positive lymphocyte, NK cell and monocyte in blood samples are measured;
   b) The multiple regression analysis using OKIa1 positive lymphocyte as dependent variable and using NK cell and monocyte as independent variables is carried out;
   c) The respective partial regression coefficients of NK cell and monocyte are determined and the significances are tested;
   d) The multiple correlation coefficient is determined and the significance is tested;

e) The contributions of NK cell and monocyte are determined; and f) The correlations between OKIa1 positive lymphocyte, NK cell and monocyte are determined.

4. A method of measuring immunokinetics through blood analysis, characterized by carrying out the following process steps (a)–(f) to assess the function of NK cell and monocyte on activated suppression inducer/helper and activated suppressor/cytotoxic T lymphocytes:

a) The counts of activated suppression inducer/helper and activated suppressor/cytotoxic T lymphocytes, NK cell and monocyte in blood samples are measured:

b) The multiple regression analysis using the sum of activated suppression inducer/helper and activated suppressor/cytotoxic T lymphocytes as dependent variable and NK cell and monocyte as independent variables is carried out;

c) The respective partial regression coefficients of NK cell and monocyte are determined and the significances are tested;

d) The multiple correlation coefficient is determined and the significance is tested;

e) The contributions of NK cell and monocyte are determined; and f) The correlations of the sum of activated suppression inducer/helper and activated suppressor/cytotoxic T lymphocytes with NK cell and monocyte are determined.

5. A method of measuring immunokinetics through blood analysis, characterized by carrying out the following process steps (a)–(g) to assess the function of NK cell and monocyte on activated B lymphocyte:

a) The counts of monocyte, NK cell, OKIa1 positive lymphocyte, and activated suppression inducer/helper and activated suppressor/cytotoxic T lymphocytes in blood samples are measured;

b) Activated B lymphocyte count is calculated by subtracting from the count of OKIa1 positive lymphocyte that of activated suppression inducer/helper T lymphocyte and that of activated suppressor/cytotoxic T lymphocyte;

c) The multiple regression analysis using activated B lymphocyte as dependent variable and NK cell and monocyte as independent variables is carried out;

d) The respective partial regression coefficients of NK cell and monocyte are determined and the significances are tested;

e) The multiple correlation coefficient is determined and the significance is tested;

f) The contributions of NK cell and monocyte are determined; and g) The correlations of activated B lymphocyte with NK cell and monocyte are determined.

6. A method of measuring immunokinetics through blood analysis, characterized by carrying out the following process steps (a)–(d) to obtain standardized partial regression coefficients and multiple correlation coefficients and plotting the coefficients on coordinates to prepare graphs for assessment:

a) The counts of monocyte, NK cell OKIa1, positive lymphocyte, helper and suppression inducer T lymphocytes and activated suppression inducer/helper T lymphocyte in blood samples are measured;

b) The standardized partial regression coefficients of helper and activated suppression inducer/helper T lymphocytes are determined by the multiple regression analysis, using monocyte as dependent variable and helper and activated suppression inducer/helper T lymphocytes as independent variables, to obtain the correlations of monocyte with helper and activated suppression inducer/helper T lymphocytes;

c) The standardized partial regression coefficients of suppression inducer and activated suppression inducer/helper T lymphocytes are determined by the multiple regression analysis using NK cell as dependent variable and suppression inducer and activated suppression inducer/helper T lymphocytes as independent variables to obtain the correlations of NK cell with suppression inducer and activated suppression inducer/helper T lymphocytes; and d) The standardized partial regression coefficients of NK cell and monocyte are determined by the multiple regression analysis using OKIa1 positive lymphocyte as dependent variable and NK cell and monocyte as independent variables to obtain the correlations of OKIa1 positive lymphocyte with NK cell and monocyte.

7. A method of measuring immunokinetics through blood analysis, characterized carrying out the following process steps (a)–(f) to obtain standardized partial regression coefficients and multiple correlation coefficients and plotting the coefficients on coordinates to prepare graphs for assessment:

a) The counts of monocyte, NK cell, OKIa1 positive lymphocyte, activated suppression inducer/helper and activated suppressor/cytotoxic T lymphocytes, and helper and suppression inducer T lymphocytes in blood samples are measured;

b) The standardized partial regression coefficients of helper and activated suppression inducer/helper T lymphocytes are determined by the multiple regression analysis using monocyte as dependent variable and helper and activated suppression inducer/helper T lymphocytes as independent variables to obtain the correlations of monocyte with helper and activated suppression inducer/helper T lymphocytes;

c) The standardized partial regression coefficients of suppression inducer and activated suppression inducer/helper T lymphocytes are determined by the multiple regression analysis using NK cell as dependent variable and suppression inducer and activated suppression inducer/helper T lymphocytes as independent variables to obtain the correlations of NK cell with suppression inducer and activated suppression inducer/helper T lymphocytes;

d) The standardized partial regression coefficients of NK cell and monocyte are determined by the multiple regression analysis using OKIa1 positive lymphocyte as dependent variable and NK cell and monocyte as independent variables to obtain the correlations of OKIa1 positive lymphocyte with NK cell and monocyte;

e) The standardized partial regression coefficients of NK cell and monocyte are determined by the multiple regression analysis using the sum of activated suppression inducer/helper and activated suppressor/cytotoxic T lymphocytes as dependent variable and NK cell and monocyte as independent variables to obtain the correlations of activated T lymphocyte with NK cell and monocyte; and f) Activated B lymphocyte count is calculated by subtracting the counts of activated suppression inducer/helper and activated suppressor/cytotoxic T lymphocytes from the OKIa1 positive lymphocyte count and the standardized partial regression coefficients of NK cell and monocyte are determined by the multiple regression analysis using activated B lymphocyte as dependent variable and NK cell and monocyte as independent variables to obtain the correlations of activated B lymphocyte with NK cell and monocyte.

8. A method of measuring and assessing immunokinetics through blood analysis, characterized by carrying out the following process steps (a)–(f) and assessing integrated T cell immunokinetics on the basis of the resultant T cell immunokinematograms:

a) The counts of CD3, CD4 and CD8 positive lymphocytes, helper, suppression inducer, suppressor and cytotoxic T lymphocytes, activated suppression inducer/helper and activated suppressor/cytotoxic T lymphocytes, NK cell and monocyte in blood samples are measured;

b) The multiple regression analysis using activated suppressor/cytotoxic T lymphocyte as dependent variable and activated suppression inducer/helper, helper, suppression inducer, cytotoxic and suppressor T lymphocytes, CD3, CD4 and CD8 positive lymphocytes, monocyte and NK cell as independent variables is carried out;

c) The respective contributions of activated suppression inducer/helper, helper, suppression inducer, cytotoxic and suppressor T lymphocytes, CD3, CD4 and CD8 positive lymphocytes, NK cell and monocyte against activated suppressor/cytotoxic T lymphocyte is determined;

d) The contributions of activated suppression inducer and activated helper T lymphocytes are calculated by allotting the contribution of activated suppression inducer/helper T lymphocyte in proportion to the ratio between the contributions of suppression inducer and helper T lymphocytes;

e) The contributions of activated suppressor and cytotoxic T lymphocytes and calculated by allotting the contribution of activated suppressor/cytotoxic T lymphocyte obtained in step b) in proportion to the ratio between the contributions of suppressor and cytotoxic T lymphocytes; and f) The respective contributions obtained in steps d) to e) are converted into circular areas, and the respective circular areas are arranged in accordance with the mutual relationships among activated helper, activated suppression inducer, activated suppressor and activated cytotoxic T lymphocytes to draw T cell immunokinematograms.

9. A method of measuring and assessing immunokinetics through blood analysis, characterized by carrying out the following process steps (a)–(g) and assessing integrated T cell immunokinetics on the basis of the resultant T cell immunokinematogram:

a) The counts of helper, suppression inducer, cytotoxic and suppressor T lymphocytes, activated suppression inducer/helper and activated suppressor/cytotoxic T lymphocytes, OKIa1 positive lymphocyte, NK cell, monocyte, basophil, eosinophil and neutrophil in blood samples are measured;

b) Activated B lymphocyte count is calculated by subtracting from the OKIa1 positive lymphocyte count the activated suppression inducer/helper T lymphocyte and activated suppressor/cytotoxic T lymphocyte counts;

c) The multiple regression analysis using activated B lymphocyte as dependent variable and helper, suppression inducer, cytotoxic, suppressor, activated suppression inducer/helper and activated suppressor/cytotoxic T lymphocytes, NK cell, monocyte, basophil, eosinophil and neutrophil as independent variables is carried out;

d) The respective contributions of helper, suppression inducer, cytotoxic, suppressor, activated suppression inducer/helper and activated suppressor/cytotoxic T lymphocytes, NK cell, monocyte, basophil, eosinophil and neutrophil against activated B lymphocyte are determined;

e) The contributions of activated helper and activated suppression inducer T lymphocytes are calculated by allotting the contribution of activated suppression inducer/helper T lymphocyte in proportion to the ratio between the contributions of helper and suppression inducer T lymphocytes;

f) The contribution of activated suppressor/cytotoxic T lymphocyte obtained in step c) is allotted in proportion to the ratio between the contributions of suppressor and cytotoxic T lymphocytes to calculate the contributions of activated suppressor and activated cytotoxic T lymphocytes; and g) The respective contributions calculated in steps d), e) and f) except for the contributions of cytotoxic and activated cytotoxic T lymphocytes are converted into circular areas, and the respective circular areas are arranged in accordance with their immunologic mutual relationships to draw the B cell immunokinematograms.

In the following explanations as will be seen later, activated suppression inducer/helper, activated suppressor/ cytotoxic, helper, suppression inducer, cytotoxic, suppressor, activated suppression inducer, activated helper, activated suppressor and activated cytotoxic T lymphocytes and OKIa1 positive lymphocyte may be abbreviated to Act.si/h T, Act.s/c T, Th, Tsi, Tc, Ts, Act.Tsi, Act.Th, Act.Ts, Act.Tc and OKIa1$^+$, respectively.

In carrying out the peripheral lymphocyte measurement, blood samples are conditioned in the usual way by adding heparin, EDTA or ACD solution as an anticoagulant, and then subjected to flow cytometry.

Measurements of peripheral lymphocytes are carried out preferably with monoclonal antibodies (MoAbs) corresponding to the respective subpopulations. Examples of MoAbs which may be used include Leu-series (Becton-Dickinson Immunocytometry Systems), OK-series (Ortho Diagnostic Systems Inc.) and T-series (Coulter Corp.). There is no restriction in the choice of MoAbs, provided that they belong to the same cluster numbers of differentiation (CD). Such measurements are carried out preferably by the fluorescent antibody technique using the single or two-color flowcytometry.

In carrying out the measurement of monocyte count, blood samples are usually applied to a full-automatic hemocytometer to count all monocytes therein. Where the monocyte count is too few to carry out such measurement, however, it is measured microscopically by the use of usual blood smears. In that case, not less than 300, preferably not less than 500, white blood cells are counted, out of which the monocyte count is calculated.

After the above-mentioned measurements of peripheral lymphocyte subpopulations and monocyte, one or more, or preferably all, of the following multiple regression analyses (MRAs) (A) to (E) are carried out.

(A) The multiple regression analysis (MRA) using monocyte as dependent variable and helper and activated suppression inducer/helper T lymphocytes as independent variables is carried out.

(B) The MRA using NK cell as dependent variable and suppression inducer and activated suppression inducer/ helper T lymphocytes as independent variables is carried out.

(C) The MRA using OKIa1 positive lymphocyte as dependent variable and NK cell and monocyte as independent variables is carried out.

(D) The MRA using the sum of activated suppression inducer/helper and activated suppressor/cytotoxic T lymphocytes counts as dependent variable and NK cell and monocyte as independent variables is carried out.

(E) Activated B lymphocyte count is calculated by subtracting from OKIa1 positive lymphocyte count the sum of activated suppression inducer/helper and activated suppressor/cytotoxic T lymphocytes counts, and then the MRA using the activated B lymphocyte as dependent variable and NK cell and monocyte as independent variables is carried out.

The combination of the above-mentioned (A), (B) and (C), the combination of (A), (B) and (D) and the combination of (A), (B) and (E) are called the immunologic three-factor set, the T-cell immunologic three-factor set and the B-cell immunologic three-factor set, respectively, for the sake of convenience.

The respective correlations in (A) to (E) are indicative of special relations namely (A): recognition mechanisms for autologous tumor antigen etc.; (B): function of NK cell; (C): cooperative function between activated lymphocyte, and monocyte and NK cell; (D): cooperative function between activated T lymphocyte, and monocyte and NK cell and (E): cooperative function between activated B lymphocyte, and monocyte and NK cell, respectively. Even with the determination of at least one of correlations (A)–(E), the immunologic assessment is possible to a certain degree.

These correlations (A)–(E) are also specific to the blood sample used and therefore serve for example as indices for the discrimination between abnormality or normality, and for the therapeutic planning.

In determining such correlations, it is desirable that the respective contributions of peripheral lymphocyte subpopulations are used to draw cell immunokinematograms, for example, by converting them into the corresponding circular areas. Since monocytes infiltrate within and/or around the cancer tissue and thereafter functionally differentiate through macrophages (Mφ) into activated Mφ, the MRAs can be carried out by substituting such activated Mφ count for monocyte count, if it is possible to measure the activated Mφ count. In the cell immunokinematograms shown as examples of this invention, therefore, the contribution of activated Mφ is expressed in terms of that of monocyte for the sake of convenience.

In accordance with this invention, it becomes possible not only to easily grasp immunokinetics, but also to predict whether the patient will relapse or not in future, for example, by comparing the results of peripheral subpopulation determination in an unknown case with the corresponding data obtained with known cases or with the time-course data obtained with the same patient, whereby the diagnosis of diseases in relation to immunity against cancer or the like is facilitated and indices for therapeutic planning against cancer or the like become available.

In accordance with the invention by measuring the above-mentioned specific lymphocyte subpopulations and monocyte counts; carrying out MRAs (A)–(E) mentioned above; determining the standardized partial regression coefficients (SPRCs); and determining correlations between the respective factors as dependent variable and the respective factors as independent variable, it is possible, for example; to rapidly grasp patterns of immunokinetics in various malignancies. That is, by determining beforehand the immunokinetic patterns of normal control group, which may be represented, for example, in form of graph and comparing the patient's patterns of immunokinetics with the immunokinetic patterns of normal control group, it is possible to make a diagnosis of cancer and the like.

Different methods may be mentioned to determine such correlations: the respective multiple correlation coefficients (MCCs) obtained by MRAs (A) to (E) are plotted on three-dimensional coordinates to draw immunokinetic graphs, rader chart graphs or stack-bar graphs and so on.

Furthermore the respective standardized partial regression coefficients (SPRCs) of independent variables obtained by MRAs (A) to (E) are plotted on two- or three-dimensional coordinates to draw patterns of triangle or triangular prism. Besides these two- or three-dimensional representations, it is also possible to draw four-dimensionally represented graphs as by addition of the factor of time, significance, contribution etc.

In making these assessments, various methods, for example, (1) the comparison between disease and normal control groups or (2) the serial and time-dependent comparison in the same patient, may be adopted.

Furthermore, according to the present invention, it is possible to assess integrated immunokinetics by drawing cellular immunokinematograms as mentioned in items 8. and 9. above.

The cellular immunokinematograms in items 8. and 9. above are T cell and B cell immunokinematograms, respectively. Taking as examples FIGS. 1A–1C, 2A–2C representations, as well as their meanings in terms of the monocyte →Act.Th and NK cell →Act.Tsi processes, in the T cell immunokinematogram will be explained below:

⁕: There is no significant correlation in the MRA between monocyte and helpers (Th and Act.si/h T). It immunologically means that the antigen recognition mechanism is impaired, hypofunctional or non-functioning.

→: In the same MRA as the above-mentioned, there is achieved for the first time a significance correlation therebetween ($p<0.05$) and the partial regression coefficient (PRC) of Act.si/h T must always be positive, because both the precursor Th and its active type, namely Act.si/h T, must be positively involved in the functional promotion of monocyte and especially in view of the fact that the active type performs the stronger function. It immunologically indicates that the antigen recognition mechanism are somewhat hyperfunctional.

⇉: In the MRA, monocyte achieves a significant correlation ($p<0.05$) only with and the PRC of Act.si/h T is always positive. It immunologically is indicative of a moderately hyperfunctional state of the antigen recognition mechanism.

⇛: In the MRA, monocyte achieves a significant correlation ($p<0.01$) only with Act.si/h T and the PRC likewise is positive. It immunologically is indicative of an ultra-hyperfunctional state.

⇢: In the MRA, monocyte barely achieves a significant correlation ($p<0.05$) only with both of Th and Act.si/h T 0.05 of P-value and the PRC of Act.si/h T is negative. It immunologically indicates a suppression of the differentiation from monocyte to macrophage (Mφ), especially a suppressive function of Mφ against helpers, namely a suppressive function on the antigen recognition mechanism.

⇸: In the MRA, monocyte achieves a significant correlation ($p<0.05$) only with Act.si/h T but its PRC is negative. It immunologically means a moderate hyperfunction of suppressive Mφ, namely a moderate suppression of the antigen recognition mechanism.

⇻: In the MRA, monocyte achieves a significant correlation ($p<0.01$) only with Act.si/h T and its PRA is negative. It immunologically means an extreme suppression of the antigen recognition mechanism.

⁕: There is no significant correlation in the MRA between NK cell and suppression inducers (Tsi, Act.si/h T), and it immunologically means an impaired, hypofunctional or non-functioning suppression against Act.Tsi. Because these correlations are the measurement of the suppressive function of NK cell against Act.Tsi, this symbol was used in all cases where the PRC of Act.si/h T is negative regardless of whether significant or not.

__: In the MRA, NK cell achieves a significant correlation (p<0.05) only with both Tsi and Act.si/h T and the PRC of Act.si/h T is positive. It immunologically means a suppressive function against Act.Tsi.

__: In the MRA between NK cell, and Tsi and Act.si/h T, NK cell achieves a significant correlation (p<0.05) only with Act.si/h T and the PRC of Act.si/h T is positive. It immunologically means a moderately suppressive function of NK cell.

__: In the MRA between NK cell, and Tsi and Act.si/h T, NK cell achieves a significant correlation (p<0.01) only with Act.si/h T and the PRC of Act.si/h T is positive. It immunologically means an extremely suppressive function of NK cell.

The following will explain how to calculate activated B lymphocyte count, with reference to B-cell immunokinematograms obtained by item 9. above.

OKIa1 positive lymphocyte count is measured by single-color flow cytometry, where granulocytes, namely neutrophil, eosinophil and basophil, monocyte and lymphocyte are automatically separated. In carrying the measurement, the gate is set so that only lymphocyte count is obtained. The ratio of lymphocyte positive when stained with OKIa1 MoAb is automatically measured on a flow cytometer. Therefore, almost all of the OKIa1 positive cells are lymphocytes.

The OKIa1 positive cells are basically expressed as T and B lymphocytes, a part of NK cells and monocyte but monocytes are completely excluded because the gate for monocyte is off at the measurement of OKIa1 positive lymphocytes. The problem is the partly-included NK cells, but their ratio is supposed to be low and therefore may be neglected for the purpose of statistic treatment. Thus, it is supposed that the majority of the OKIa1 positive cells are T and B cells. The lymphocytes expressed as the OKIa1 antigen are considered to be activated lymphocyte and the OKIa1 antigen may be taken as being almost identical to HLA-DR, a major histocompatibility antigen class II. Therefore, activated T lymphocyte (Act.T) count is calculated as Act.si/h T count plus Act.s/c T count. Activated B lymphocyte (Act.B) count is calculated as OKIa1 positive lymphocyte count minus Act.T count. This is because the lymphocyte consists only of the two types, i.e. T and B lymphocytes.

For the strict determination of activated B lymphocyte count, MoAbs directed to several other kinds of B lymphocyte should be used in staining, which, however, will increase cost as well as the time and blood sample volume required for investigation. Therefore, from the view point of cost and complexity as well as from clinical practicality, OKIa1 positive lymphocyte count minus activated T lymphocyte count, both counts obtained upon the measurement of T cell immunity, are taken, for the sake of convenience, as measured values for activated B lymphocyte. Whenever, although rare, the calculated value of Act.B count becomes minus, the count of Act.B is regarded as zero. After those procedures, B cell immunokinematograms can be drawn.

The assessment of B cell immunity is useful and convenient for the understanding, for example, of immunities relating to the cellular system producing antibodies, as well as immunities involved in allergy and neutrophil-based immunities involved in bacterial infections.

The concrete methodology will now be explained below. In the same manner as described above for T cell immunity, the MRA using Act.B as dependent variable and monocyte, Th, Tsi, Act.si/h T, Tc, Ts, Act.s/c T, NK cell, basophil, eosinophil and neutrophil as independent variables is carried out and the contribution of each independent variable is determined. As in the case of T cell immunity, based on the immunologic relationships with Act.B, the respective contributions converted into the corresponding circular areas are arranged. In carrying out this, the contributions of Act.Th, Act.Ts and Act.Tsi are determined not directly but by dividing the cuntributions of Act.si/hT and Act.s/cT in accordance with ratio of their precursors, i.e. Th, Tsi, Tc and Ts: Act.Th (%)=Act.si/h T×{Th+(Th+Tsi)}, Act.Tsi (%)= Act.si/h T×{Tsi+(Th+Tsi)}, and Act.Ts (%)=Act.s/cT×{Ts+(Tc+Ts)}.

As for the relations in terms of the monocyte →Act.Th and NK cell →Act.Tsi processes, the MRAs carried out for drawing T cell immunokinematograms and their results are adopted. Besides them, the relations between Act.B and helpers (Th and Act.si/h T) are assessed by the MRA using Act.B as dependent variable and Th and Act.si/h T as independent variables, and those between neutrophil and helpers, between eosinophil and helpers and between basophil and helpers, are assessed by the MRAs using neutrophil, eosinophil and basophil, respectively, as dependent variables and Th and Act.si/h T as independent variables.

According to these MRAs, it is possible, while drawing B cell immunokinetograms, to express the degree of the respective mutual relationships with concrete figures. The figures (in %) used are expressed in terms of the contribution of Act.si/hT in the respective MRAs, as is the case with the monocyte →Act.Th and NK cell →Act.Tsi processes. Furthermore, the symbols in these immunokinematograms are used to mean the following:

∗: There is no significance in the MRA and no immunologic hyperfunction is detected.

__: In the MRA, there is a significant correlation (p<0.05 by f-test) only with both Th and Act.si/h T and the PRC of Act.si/h T must be positive. If the PRC of Act.si/h T is negative regardless of there being such significant correlation with both of Th and Act.si/h T, the symbol ∗ must be used because both of precursors Th and Act.si/h T including its active type must be positively involved in the immunologic promotion. It means some degree of hyperfunction immunologically.

__: In the MRA, there is significant correlation (p<0.05) only with Act.si/h T. It immunologically means a hyperfunction.

__: In the MRA, there is a significant correlation (p<0.01) only with Act.si/h T. It immunologically means an extreme hyperfunction.

In the accompanying drawings, these four patterns of symbol will be shown.

Thus, FIG. 7 is taken as an example to explain cellular immunokinematograms and immunologic three-factor sets.

In the left of FIG. 7, a T cell immunokinematogram is shown and the abbreviations and symbols therein are used to mean the following: →: differentiation and maturation; __: establishment of antigen recognition mechanism (p<0.05 by f-test); __: promotion or acceleration, ←: suppression; __: no suppressive function of NK cell; __: cytotoxicity; ●: 0.1%≧of contribution; (%): the contribution of activated suppression inducer/helper T cell versus monocyte or NK cell; γ: multiple correlation coefficient.

In the right of FIG. 7, the immunologic three-factor sets are shown and the abbreviations and symbols therein are used to mean the following: Δ: The relation of monocyte versus helper and activated suppression inducer/helper T lymphocytes: □: The relation of NK cell versus suppression inducer and activated suppression inducer/helper T lymphocytes; ●: The relation of OKIa1 positive lymphocyte versus monocyte and NK cell; o: The relation of activated T lymphocyte versus monocyte and NK cell; and ⊙: The relation of activated B lymphocyte versus monocyte and NK cell.

The invention will be explained in more detail with reference to some examples.

EXAMPLES

Example 1

Measurement of Cellular Immunokinetics Based upon Autologous Tumor Antigen Recognition Mechanism in Metastatic Renal Cancer Patients

MATERIALS

Twenty-four patients admitted and treated in the Urological Department of the Cancer Institute Hospital from June 1983 to December 1988 were used. Three cases among them had been treated by other clinics initially, in respect of which the detailed information on the staging and their histological diagnoses at the initial examination were not available. The staging and histological grading were conducted according to the criteria of the General Rule for Clinical and Pathological Studies on Renal Cell Carcinoma (The Japanese Urological Association, The Japanese Pathological Society and Japan Radiological Society). The majority of patients had metastases mostly to lungs and bones.

All of them were treated with human lymphoblastoid interferon (HLBI: Sumiferon®, Sumitomo Pharmaceutical Co., Ltd., Osaka, Japan). As a rule HLBI was dosed everyday intramuscularly starting with a dose of 3 million units, which were increased to 6, 9 and 12 million units, respectively, every week, and the maximal tolerable dose was maintained twice weekly. Some patients had the maintenance dose everyday, or 3 to 5 times weekly. In some cases, the radiotherapy and surgical resection were applied to the metastatic site concomitantly. Further, as oral anticancer agent, UFT (Tegafur/Uracil formulation, Taiho Yakuhin Kogyo, Co., Ltd. JAPAN) or doxifluridine (5'-DFUR: Furtulon®, Nippon Roche Co., Ltd., Tokyo, Japan) was used combinedly. Further, as intensive chemotherapy vinblastine and adriamycin were additionally dosed to 3 cases. Arterial embolization was performed at the primary lesion or local recurrence for a case with T4 of local extension inoperable together with metastases to the lung and liver, or another case with local recurrence 10 years after operation of the primary lesion and metastasis to the lung.

In addition to the treatment with HLBI, OK-432 (Picibanil®, Chugai Pharmaceutical Co., Ltd., Tokyo, Japan) was given as another BRMs in some cases, and, gene re-combinated γ-interferon (γ-IFN: supplied by Daiichi Seiyaku Co., Ltd., Tokyo, Japan), or $N^2$-(N-acetylmuramyl-L-alanyl-D-isoglutamyl)-$N^6$-stearoyl-L-lysine (MDP-Lys (L18): supplied by Daiichi Seiyaku Co., Ltd.), a derivative of muramyl dipeptide which is a component of the cell wall skeleton in tubercle bacillus, was also additionally applied in some cases. OK-432 was given subcutaneously everyday starting with 0.5 KE (Klinische Einheit) and increasing doses every 3 days to 1,2 and 3 KE, respectively and maintained at 3 KE twice weekly. MDP-Lys (L18) was maintained by subcutaneous injection at 200 mcg once weekly.

From the outset of the treatment with HLBI, peripheral lymphocyte subsets were determined with the passage of time, and as a rule a determination was always made at the addition of further treatment or at the change of treatment. Further, the determination was performed upon sufficient recovery of the bone marrow function, where that was strongly suppressed due to intensive chemotherapy. The therapeutic effect was evaluated according to the criteria for cancer chemocherapeutic evaluation of the Ministry of Health and Welfare. The subsets were measured simultaneously with the evaluation of clinical effects and when the lesions were unchanged or decreased their results were classified as the stable or improved group, and those measured at increase of tumor size by more than 25% or occurrence of new lesion were classified as the progressive disease (PD) group. When evaluated once as PD, until the next time of evaluation of the lesion having increased by more than 25% and/or a new lesion having occurred again, the results of subsets measured during that time were classified as the stable or improved group. As a rule, the measurement of subsets was performed monthly and when the lesion is stabilized, once in 2 or 3 months.

Meanwhile, as the normal control, peripheral lymphocyte subsets of 40 healthy volunteers without history of malignant neoplasm such as cancer, in their age ranging from 31 to 78 years, 55.4±13.0 years (mean±S.D.), consisting of 17 females and 23 males, were measured.

DETERMINATION OF PERIPHERAL LYMPHOCYTE SUBSETS AND MONOCYTE

As a rule, lymphocytes were isolated from the heparinized blood collected out of the cubital vein. Upon collection and removal of red blood cells with a defined hemolytic agent, lymphocytes were stained with flurorescein isothiocyanate—or phycoerythrin-labelled monoclonal antibody, and then determined by the single-color flow cytometry (Spectrum III, Ortho Diagnostic Systems Inc., New Jersey, USA) and the two-color flow cytometry (FACS analyzer* Consort 30, Becton Dickinson Immunocytometry Systems, Mountain View, Calif.).

Lymphocytes positive to OKT3, OKT4, OKT8 and OKIa1 monoclonal antibodies (Ortho Diagnostic Systems Inc.) were determined on a single-color flow cytometer, and cells positive to Leu3a$^+$•Leu8$^-$ (helper T lymphocytes: Th), Leu3a$^+$•Leu8a$^+$ suppression inducer T lymphocytes: Tsi), Leu2a$^+$•Leu15$^-$ (cytotoxic T lymphocytes: Tc), Leu2a$^+$•Leu15$^+$ (suppressor T lymphocytes: Ts), Leu7$^-$•Leu11c$^+$ (natural killer cells: NK cells), Leu3a$^+$•HLA-DR$^+$ (activated suppression inducer/helper T lymphocytes: Act.si/h T) and Leu2a$^+$•HLA-DR$^+$ (activated suppressor/cytotoxic T lymphocytes: Act.s/c T), were determined on a two-color flow cytometer, using monoclonal antibodies against Leu and HLA-DR manufactured by Becton Dickson Immunocytometry Systems.

Lymphocytes and monocytes in the peripheral blood were counted on a full-automatic hemocytometer (Coulter Electronics Corporation, Florida, USA). Meanwhile, when lymphocytes and monocytes were too few to count in the peripheral blood, it was counted microscopically after usual smear staining. The real number of each subset ($/mm^3$) was calculated from the number of peripheral lymphocytes multiplied by each subset in percentage obtained upon the flow cytometry. In the normal control group, the measurement was performed 40 times with 40 cases, and in the PD group it was performed a total of 50 times with 20 cases. In the stable or improved group, it was performed a total of 93 times with 24 cases. The results of the respective lymphocyte and monocyte counts are shown in Table 1.

TABLE 1

| Unit:/mm³ | Normal control group (n = 40) | Progressive disease group (n = 50) | Stable or improved group (n = 93) |
|---|---|---|---|
| OKT3 | 1341* ± 413 | 742 ± 454 | 880 ± 407 |
| OKT4 | 853 ± 295 | 495 ± 324 | 551 ± 275 |
| OKT8 | 606 ± 239 | 315 ± 235 | 377 ± 194 |
| OKIaI | 588 ± 310 | 300 ± 268 | 416 ± 274 |
| Th | 423 ± 155 | 311 ± 222 | 346 ± 182 |
| Tsi | 387 ± 170 | 169 ± 147 | 192 ± 130 |
| Tc | 424 ± 180 | 237 ± 176 | 288 ± 167 |
| Ts | 123 ± 92 | 45 ± 57 | 59 ± 44 |
| Act.si/hT | 26.8 ± 19.5 | 18.4 ± 17.7 | 32.2 ± 21.3 |
| Act.s/cT | 19.5 ± 17.7 | 12.8 ± 13.7 | 42.7 ± 40.1 |
| NK cell | 201 ± 106 | 95 ± 75 | 160 ± 117 |
| Monocyte | 330 ± 142 | 396 ± 260 | 396 ± 243 |
| Act.T | 46.2 ± 35.4 | 31.2 ± 28.5 | 74.9 ± 56.0 |
| Act.B | 542 ± 294 | 269 ± 265 | 342 ±0 265 |

*Mean ± SD

MULTIPLE REGRESSION ANALYSIS OF MONOCYTE AND EACH LYMPHOCYTE SUBSET IN THE PERIPHERAL BLOOD

For the purpose of knowing the mutual relationship between each lymphocyte subset and monocyte in the peripheral blood, multiple regression analysis was performed.

The multiple regression analysis was conducted to see whether or not the multiple regression equation is established in the respective groups (i.e. the normal control, progressive disease, and stable or improved groups), using Act.s/c T as dependent variable and monocyte and each peripheral lymphocyte subset as dependent variables. Significant difference of partial regression coefficients was checked by t-test, and that of multiple correlation coefficients by f-test. Further, significant difference of simple correlation coefficients between subpopulations was examined by t-test.

MULTIPLE REGRESSION ANALYSIS USING Act.s/c T AS DEPENDENT VARIABLE AND EACH SUBSET AND MONOCYTE AS INDEPENDENT VARIABLES a. Normal Control Group

In the matrix of simple correlation coefficient Act. s/c T showed a correlation of as strong as r=0.807 (p<0.01) with Act.si/h T. Further, NK cells showed no correlation with either of them, and monocytes were related to Th (r=0.246), and to Act.si/h T (r=0.344, p<0.05).

The multiple regression equation was significantly established for Act.s/c T (r=0.92893, p<0.01; constant: 0.27972). It was also established significantly in terms of partial regression coefficient with the subsets Leu11$^+$ (p<0.05), Tc (p<0.05), Ts (p<0.05) and Act.si/h T (p<0.01). The contributions were noted to be 0.83, 0.09, 3.73, 7.71, 65.05, 1.79 and 1.55% for Th, Tsi, Tc, Ts, Act.si/h T, monocytes and NK cells, respectively, and the total contribution was 86.29%. These results are shown in Table 2.

TABLE 2

| (n = 40) Independent variables | OKT3 | OKT4 | OKT8 | OKIaI | NK cell | Th | Tsi | Tc | Ts | Act. si/hT | Act. s/cT | Monocyte | Partial regression coefficient | Contribution (%) |
|---|---|---|---|---|---|---|---|---|---|---|---|---|---|---|
| OKT3 | | 0.835** | 0.802** | 0.625** | 0.230 | 0.783** | 0.529** | 0.727** | 0.497** | 0.380* | 0.331* | 0.132 | 0.00649 | 0.10 |
| OKT4 | 0.835** | | 0.427** | 0.441** | 0.287 | 0.682** | 0.809** | 0.361* | 0.268 | 0.339* | 0.109 | 0.08 | −0.03621* | 4.73 |
| OKT8 | 0.802** | 0.427** | | 0.683** | 0.221 | 0.593** | 0.129 | 0.837** | 0.661** | 0.348* | 0.473** | 0.240 | −0.02342 | 0.61 |
| OKIaI | 0.625** | 0.441** | 0.683* | | 0.182 | 0.449** | 0.242 | 0.512** | 0.597** | 0.472** | 0.460** | 0.309 | −0.00026 | 0.00 |
| NK cell | 0.230 | 0.287 | 0.221 | 0.182 | | 0.072 | 0.156 | 0.017 | 0.227 | 0.162 | 0.218 | 0.297 | 0.03956* | 1.55 |
| Th | 0.783** | 0.682** | 0.593** | 0.449** | 0.072 | | 0.346* | 0.543** | 0.271 | 0.418** | 0.317* | 0.246 | 0.01838 | 0.83 |
| Tsi | 0.529** | 0.809** | 0.129 | 0.242 | 0.156 | 0.346* | | 0.092 | 0.196 | 0.208 | −0.005 | −0.087 | 0.00799 | 0.09 |
| Tc | 0.727** | 0.361* | 0.837** | 0.512** | 0.017 | 0.543** | 0.092 | | 0.372* | 0.130 | 0.310 | 0.095 | 0.03714* | 3.73 |
| Ts | 0.497** | 0.268 | 0.661** | 0.597** | 0.227 | 0.271 | 0.196 | 0.372* | | 0.425** | 0.596** | 0.100 | 0.05911* | 7.71 |
| Act. si/hT | 0.380* | 0.339* | 0.348* | 0.472** | 0.162 | 0.418** | 0.208 | 0.130 | 0.425** | | 0.807** | 0.344* | 0.73338** | 65.05 |
| Act. s/cT | 0.331* | 0.109 | 0.473** | 0.460** | 0.218 | 0.317* | −0.005 | 0.310 | 0.596** | 0.807** | | 0.204 | — | — |
| Monocyte | 0.132 | 0.080 | 0.240 | 0.309 | 0.297 | 0.246 | −0.087 | 0.095 | 0.100 | 0.344* | 0.204 | | −0.01738 | 1.79 |
| Constant | | | | | | | | | | | | | 0.27972 | 86.29 (Sum) |

(Dependent variable = Act.s/cT)

Multiple correlation coefficient = 0.92893 (p < 0.01)
*p < 0.05
**p < 0.01 (t test)

b. Progressive Disease Group

In the matrix of simple correlation coefficient Act.s/c T was correlated with Act.si/h T (r=0.633, p<0.01), while NK cells correlated with Tsi (r=0.818, p<0.01), Act.si/h T (r=0.507, p<0.01) and monocytes (r=0.285, p<0.05), respectively. Monocytes were correlated with Th (r=0.363, p<0.01), and Act.si/h T (r=0.109).

Act.s/c T, at r=0.80687 (p<0.01) and constant=6.45252, showed establishment of the multiple regression equation with significant partial regression coefficients of OKT8 (p<0.05), and Act.si/h T (p<0.01), respectively. The contributions were 1.03, 0.29, 4.17, 13.25, 40.01, 3.82 and 0.14% for Th, Tsi, Tc, Ts, Act.si/h T, monocytes and NK cells, respectively and the total contribution was 65.11%. These results are shown in Table 3.

p<0.01), Act.si/h T (r=0.4, p<0.01) and monocytes (r=0.096), respectively. Monocytes were correlated with Th (r=0.283, p<0.01), and Act.si/h T (r=0.209), respectively.

Act.s/c T, at r=0.75889 (p<0.01) and constant=3.15737, showed establishment of the multiple regression equation with significant partial regression coefficients of OKT4 (p<0.05), NK cells (p<0.05) and Act.si/h T (p<0.01), respectively. The contributions were 0.31, 0.73, 3.9, 1.2, 39.45, 0.43 and 10.15% for Th, Tsi, Tc, Ts, Act.si/h T, monocytes and NK cells, respectively and the total contribution was 57.6%. These results are shown in Table 4.

TABLE 3

(n = 50) (Dependent variable = Act.s/cT)

| Independent variables | OKT3 | OKT4 | OKT8 | OKIal | NK cell | Th | Tsi | Tc | Ts | Act. si/hT | Act. s/cT | Mono- cyte | Partial regression coefficient | Contribution (%) |
|---|---|---|---|---|---|---|---|---|---|---|---|---|---|---|
| OKT3 |  | 0.966** | 0.849** | 0.792** | 0.499** | 0.88** | 0.779** | 0.839** | 0.564** | 0.308* | 0.307* | 0.38** | −0.01184 | 0.09 |
| OKT4 | 0.966** |  | 0.753** | 0.824** | 0.409** | 0.901** | 0.843** | 0.761** | 0.452** | 0.276 | 0.23 | 0.406** | 0.0637 | 0.10 |
| OKT8 | 0.849** | 0.753** |  | 0.544** | 0.645** | 0.626** | 0.497** | 0.947** | 0.768** | 0.243 | 0.43** | 0.322* | 0.01161* | 0.7 |
| OKIal | 0.792** | 0.824** | 0.544** |  | 0.254 | 0.858** | 0.681** | 0.576** | 0.185 | 0.194 | 0.126 | 0.406** | 0.01458 | 1.51 |
| NK cell | 0.499** | 0.409** | 0.645** | 0.254 |  | 0.253 | 0.264 | 0.575** | 0.818** | 0.507** | 0.574** | 0.285* | −0.00824 | 0.14 |
| Th | 0.88** | 0.901** | 0.626** | 0.858** | 0.253 |  | 0.631** | 0.621** | 0.321* | 0.234 | 0.147 | 0.363** | 0.01279 | 1.03 |
| Tsi | 0.779** | 0.843** | 0.497** | 0.681** | 0.264 | 0.631** |  | 0.563** | 0.194 | 0.284* | 0.167 | 0.266 | −0.05743 | 0.29 |
| Tc | 0.839** | 0.761** | 0.947** | 0.576** | 0.575** | 0.621** | 0.563** |  | 0.665** | 0.185 | 0.296* | 0.337* | 0.05217 | 4.17 |
| Ts | 0.564** | 0.452** | 0.768** | 0.185 | 0.818** | 0.321* | 0.194 | 0.665** |  | 0.436** | 0.603** | 0.156 | 0.05915 | 13.25 |
| Act. si/hT | 0.308* | 0.276 | 0.243 | 0.194 | 0.507** | 0.234 | 0.284* | 0.185 | 0.436** |  | 0.633** | 0.109 | 0.34678** | 40.01 |
| Act. s/cT | 0.307* | 0.23 | 0.43** | 0.126 | 0.574** | 0.147 | 0.167 | 0.296* | 0.603** | 0.633** |  | −0.08 | — | — |
| Monocyte | 0.38* | 0.406** | 0.322* | 0.406** | 0.285* | 0.363** | 0.266 | 0.337* | 0.156 | 0.109 | −0.08 |  | −0.01104 | 3.82 |
| Constant |  |  |  |  |  |  |  |  |  |  |  |  | 0.45242 | 65.11 (Sum) |

Multiple correlation coefficient = 0.80687 (p < 0.01)

*p < 0.05
**p < 0.01 (t test)

c. Stable or Improved Group

In the matrix of simple correlation coefficient Act.s/c T was correlated with Act.si/h T (r=0.628, p<0.01), while NK cells were correlated with Tsi (r=−0.114), Ts (r=0.483,

TABLE 4

(n = 93) (Dependent variable = Act.s/cT)

| Independent variables | OKT3 | OKT4 | OKT8 | OKIal | NK cell | Th | Tsi | Tc | Ts | Act. si/hT | Act. s/cT | Mono- cyte | Partial regression coefficient | Contribution (%) |
|---|---|---|---|---|---|---|---|---|---|---|---|---|---|---|
| OKT3 |  | 0.923** | 0.828** | 0.637** | 0.149 | 0.856** | 0.581** | 0.83** | 0.428** | 0.174 | 0.102 | 0.284** | 0.02189 | 0.15 |
| OKT4 | 0.923** |  | 0.618** | 0.458** | 0.007 | 0.843** | 0.703** | 0.642** | 0.377** | 0.133 | −0.038 | 0.258** | −0.09823* | 1.13 |
| OKT8 | 0.828** | 0.618** |  | 0.727** | 0.395** | 0.626** | 0.285** | 0.87** | 0.486** | 0.24* | 0.288** | 0.185 | −0.03283 | 0.15 |
| OKIal | 0.637** | 0.453** | 0.727** |  | 0.449** | 0.544** | 0.218* | 0.688* | 0.473** | 0.142 | 0.291** | 0.239* | 0.00116 | 0 |
| NK cell | 0.149 | 0.007 | 0.395** | 0.449** |  | 0.011 | −0.114 | 0.235* | 0.483** | 0.4** | 0.54** | 0.096 | 0.0878* | 10.15 |
| Th | 0.856** | 0.843** | 0.626** | 0.544** | 0.011 |  | 0.404** | 0.63** | 0.255** | 0.2* | 0.05 | 0.283** | 0.04006 | 0.31 |
| Tsi | 0.581** | 0.703** | 0.285** | 0.218* | −0.114 | 0.404** |  | 0.411** | 0.252* | −0.014 | −0.079 | 0.104 | −0.03707 | 0.73 |
| Tc | 0.83** | 0.642** | 0.87** | 0.688** | 0.235* | 0.63** | 0.411** |  | 0.347** | 0.129 | 0.221* | 0.272** | 0.06675 | 3.9 |
| Ts | 0.428** | 0.377** | 0.486** | 0.473** | 0.483** | 0.255** | 0.252* | 0.347** |  | 0.446** | 0.435** | 0.185 | 0.16116 | 1.2 |
| Act. | 0.174 | 0.133 | 0.24* | 0.142 | 0.4** | 0.2* | −0.014 | 0.129 | 0.446** |  | 0.628** | 0.029 | 0.87656** | 39.45 |

TABLE 4-continued

| (n = 93) | | | | | | | | | | | | | (Dependent variable = Act.s/cT) | |
|---|---|---|---|---|---|---|---|---|---|---|---|---|---|---|
| Independent variables | OKT3 | OKT4 | OKT8 | OKIal | NK cell | Th | Tsi | Tc | Ts | Act. si/hT | Act. s/cT | Monocyte | Partial regression coefficient | Contribution (%) |
| si/hT Act. s/cT | 0.102 | −0.038 | 0.288* | 0.291** | 0.543** | 0.05 | −0.079 | 0.221* | 0.435* | 0.628** | | −0.013 | — | — |
| Monocyte | 0.284* | 0.258* | 0.185 | 0.239* | 0.096 | 0.283* | 0.104 | 0.272** | 0.185 | 0.029 | −0.013 | | −0.01412 | 0.43 |
| Constant | | | | | | | | | | | | | 3.15737 | 57.60 (Sum) |
| Multiple correlation coefficient = 0.75889 (p < 0.01) | | | | | | | | | | | | | | |

\*p < 0.05
\*\*p < 0.01 (t test)

MULTIPLE REGRESSION ANALYSIS USING MONOCYTE AS DEPENDENT VARIABLE AND Act.si/h T AND Th AS INDEPENDENT VARIABLES a. Normal Control Group

In the normal control group monocytes singly established a relation with Act.si/h T at r=0.34396 (p<0.05). It means that the autologous tumor antigen recognition mechanism (ATARM) from monocytes to Mφ and Act.Th is established. Further, it is one of the criteria for determination in comparison with other groups that correlation is at about r=0.34396 in the normal.

b. Progressive Disease Group

Monocytes showed a multiple correlation with Th and Act.si/h T at r=0.36376 (p<0.05). However, the contribution of Act.si/h T was extremely reduced (to as low as 0.06%) as compared with the normal, and they were mainly related to Th, a precursor cell of Act.Th, it thus being shown that the ATARM was reduced extremely.

c. Stable or Improved Group

As in the progressive disease group, monocytes showed a multiple correlation at r=0.2486 (p<0.05), but the contribution of Act.si/h T was as low as 0.08% and the ATARM was reduced extremely. These results are shown in Table 5.

MULTIPLE REGRESSION ANALYSIS USING NK CELL AS DEPENDENT VARIABLE AND Act.Si/h T AND Tsi AS INDEPENDENT VARIABLES a. Normal Control Group

NK cell did not establish a relation with Act.si/h T and Tsi, which means that the activity of NK cell has not been potentiated.

b. Progressive Disease Group

NK cell established a relation only with Act.si/h T at r=0.50688 (p<0.01). This means a strong relationship with Act.Tsi, suggesting an intensified activation by the HLBI treatment.

c. Stable or Improved Group

As in the progressive disease group, NK cell established a relation only with Act.si/h T at r=0.39953 (p<0.01), suggesting an intensified activation.

These results are shown in Table 6.

TABLE 5

| Dependent variable = | Normal control group (n = 40) | | Progressive disease group (n = 50) | | Stable or improved group (n = 93) | |
|---|---|---|---|---|---|---|
| Monocyte Independent variables | Partial regression coefficient | Contribution (%) | Partial regression coefficient | Contribution (%) | Partial regression coefficient | Contribution (%) |
| Th | — | — | 0.41948* | 13.17 | 0.38468** | 8.02 |
| Act.si/hT | 2.4962* | 11.83 | 0.37159 | 0.06 | −0.32469 | 0.08 |
| Constant | 263.222 | Sum 11.83 | 258.697 | Sum 13.23 | 273.056 | Sum 8.10 |
| Multiple correlation coefficient | = 0.34396(p < 0.05) | | = 0.36376(p < 0.05) | | = 0.2846(p < 0.05) | |

\*p < 0.05
\*\*p < 0.01 (t test)

TABLE 6

| Dependent variable = | Normal control group (n = 40) | | Progressive disease group (n = 50) | | Stable or improved group (n = 93) | |
|---|---|---|---|---|---|---|
| NK cell Independent variables | Partial regression coefficient | Contribution (%) | Partial regression coefficient | Contribution (%) | Partial regression coefficient | Contribution (%) |
| Tsi | 0.08025 | 1.58 | — | — | — | — |
| Act.si/hT | 0.73532 | 2.62 | 2.15649** | 25.69 | 2.1898** | 15.96 |
| Constant | 149.825 | Sum 4.20 | 258.697 | Sum 25.69 | 273.056 | Sum 15.96 |
| Multiple correlation coefficient | = 0.20490(n.s.) | | = 0.50688(p < 0.01) | | = 0.39953(p < 0.01) | | n.s.: not significant
*p < 0.05
**p < 0.01 (t test)

MULTIPLE REGRESSION ANALYSIS USING OKIa1 POSITIVE LYMPHOCYTES AS DEPENDENT VARIABLE AND MONOCYTE AND NK CELL AS INDEPENDENT VARIABLES

Since lymphocytes and monocytes are considered to be activated upon expression of the major histocompatibility complex: Ia antigen or HLA-DR antigen, the multiple regression analysis was conducted to study contribution of the monocytes and the NK cells related to expression of Ia antigen using the OKIa1 positive lymphocytes count as dependent variable.

a. Normal Control Group

The multiple regression was not established being insignificant at r=0.32308. It means that in the normal human at r=0.32308, a contribution of the monocytes 9.54% and that of the NK cells 0.89%, is maintained a homeostasis, thus immunologically monocytes and NK cells are participating neither in activation nor in suppression of expression of Ia antigen. Such multiple correlation coefficient and contributions are the standard values to estimate whether monocytes and NK cells have been activated or suppressed.

b. Progressive Disease Group

The expression of Ia antigen was dependent significantly on monocytes compared with the normal, and the contribution of NK cells was also higher, which is considered to be due to the α-IFN treatment.

c. Stable or Improved Group

The contributions and multiple correlation coefficient were even higher, showing a stronger dependence on monocytes and NK cells. This is considered to be due to the α-IFN treatment, etc., but functions of monocytes and NK cells were more activated than in the normal.

Those results are shown in Table 7.

TABLE 7

| Dependent variable = | Normal control group (n = 40) | | Progressive disease group (n = 50) | | Stable or improved group (n = 93) | |
|---|---|---|---|---|---|---|
| OKIa1 Independent variables | Partial regression coefficient | Contribution (%) | Partial regression coefficient | Contribution (%) | Partial regression coefficient | Contribution (%) |
| Monocyte | 0.61131 | 9.54 | 0.37391** | 16.47 | 0.22353* | 20.19 |
| NK cell | 0.289 | 0.89 | 0.53554 | 2.09 | 1.01107** | 3.87 |
| Constant | 328.051 | Sum 10.43 | 100.99 | Sum 18.56 | 166.253 | Sum 24.06 |
| Multiple correlation coefficient | = 0.32308(n.s.) | | = 0.43076(p < 0.01) | | = 0.4906(p < 0.01) | | n.s.: not significant
*p < 0.05
**p < 0.01 (t test)

The foregoing results confirm that, in the normal control group which is not cancer-bearing, neither activation nor suppression takes place and no activities of monocytes and NK cells related to expression of Ia antigen are recognized.

However, in the PD group and the stable or improved group, where influence of α-IFN is considered to be great, it was demonstrated that compared with the normal control group functions of monocytes and NK cells were significantly accelerated to activate lymphocytes by expression of Ia antigen. It has also been indicated in specific figures that in the PD group two functions of monocytes and NK cells are more accelerated compared with the normal, but that it is impossible to improve the disease with the multiple correlation coefficient or contributions as shown in Table 7. At least to stabilize or improve the disease, as noted in the results of multiple regression analysis for the stable or improved group in Table 7 (contribution of monocytes 20.19% and that of NK cells 3.87%), it can be understood that compared with the normal control, an activation a little over 2 times for monocytes and that a little over 4 times for NK cells, are required.

Thus, according to the immunokinetic measurement of this invention, namely by performing any of the above-mentioned procedures (A)–(C) to determine the mutual relationship between each factor as dependent variable and the respective factors as independent variables, it is possible to estimate to which one of the groups (i.e. the normal control, progressive disease and stable or improved groups) the result of measurement with a patient under therapy belongs, and to determine whether the treatment is appropriate or not.

For the purpose of knowledge of more detailed immunokinetics, cellular immunokinematograms should be drawn.

CELLULAR IMMUNOKINEMATOGRAM

For making kinematograms of cellular immunity, contributions of each subset and monocytes obtained by the multiple regression analysis using Act.s/c T as dependent variable were arranged directly as areas of the circle based on the mutual relationship and process of differentiation and maturation of each subset generally established nowadays basically and clinically. Meanwhile, it has not been clarified specifically yet up to date to which subset the NK cells are related most strongly, and what its major activity is. Therefore, based on the simple correlation coefficient matrix of the analytical results obtained in this study, it was supposed to have a mutual relationship with the lymphocytes showing the strongest correlation. For these reasons, in practice, contribution of Act.si/h T was partitioned according to those of the respective precursor cells, Tsi and Th, to calculate contributions of Act.Tsi and Act.Th. In the same manner the total contribution of Act.s/c T was divided in proportion to the ratio of Ts and Tc, to calculate contributions of Act.Ts and Act.Tc. Further, in the case of M$\phi$, the contribution of monocytes as such was used as that of M$\phi$.

The contributions of Act.Th, Act.Tc, Act.Ts and Act.Tsi were calculated as follows. Act.Th in the normal control is determined by [Th/(Th+Tsi)]×Act.si/hT. The contribution of each subset from Table 2 is substituted for the corresponding term to obtain [0.83+(0.83+0.09)]×65.05=58.69 (%). In the same way, Act.Tc is [Tc/(Tc+Ts)]×Act.s/cT, and substitution of values gives [3.73+(3.73+7.71)]×86.29=28.13 (%). Thus the contributions of Act.Tsi and Act.Ts were calculated and expressed as areas of circle, and the circular areas were arranged in accordance with the mutual relations between different peripheral lymphocyte subsets to obtain cellular kinematograms, as shown in FIGS. 1A–1C.

Immunokinetics between the groups can be grasped at a glance from such cellular immunokinematograms. Such kinematograms make it possible to better understand behaviors of immunologically competent cell in each group, thus being shown to be useful in treatment including evaluation of the therapeutic effect. Thus, from determinations of peripheral lymphocyte subsets are obtainable practical and easy-to-understand kinematograms, which make it possible to reveal a series of cellular immunokinetics following the ATARM.

Example 2

Measurement of Cellular Immunokinetics Based upon Autologous Tumor Antigen Recognition Mechanism in Easily-Recurrent Superficial Bladder Cancer Patients

MATERIALS

The subjects in this study consisted of 59 such patients who were admitted and treated in the Department of Urology, Cancer Institute Hospital between February 1977 and December 1985. Of 59 patients, 27 experienced recurrence less than three years after the previous transurethral resection of tumor (TUR), and peripheral lymphocyte subsets were determined when such recurrence was confirmed. The remaining 32 including nine patients with the history of recurrence had experienced no recurrence for three years or more after the initial TUR or treatment of recurrent cancer. Peripheral lymphocyte subsets were determined in these cases at the final observation. The former and latter patients were classified as the recurrent and not-recurrent groups, respectively and the results of determination were analyzed. As measured values for the normal control group were adopted those obtained with the normal control group in Example 1.

DETERMINATION OF PERIPHERAL LYMPHOCYTE SUBPOPULATIONS AND MONOCYTE

The same procedure as in Example 1 was followed to obtain the values as shown in Table 8.

TABLE 8

| Unit:/mm$^3$ | Normal control group (n = 40) | Recurrent group (n = 27) | Not-recurrent group (n = 32) |
|---|---|---|---|
| OKT3 | 1341 ± 413 | 1349 ± 353 | 1506 ± 600 |
| OKT4 | 853 ± 295 | 894 ± 348 | 874 ± 358 |
| OKT8 | 606 ± 239 | 624 ± 294 | 750 ± 346 |
| OKIa1 | 588 ± 310 | 470 ± 207 | 544 ± 380 |
| Th | 423 ± 155 | 505 ± 237 | 480 ± 247 |
| Tsi | 387 ± 170 | 352 ± 183 | 367 ± 217 |
| Tc | 424 ± 180 | 468 ± 283 | 607 ± 382 |
| Ts | 123 ± 92 | 101 ± 68 | 144 ± 86 |
| Act.si/hT | 26.8 ± 19.5 | 46.6 ± 38.9 | 52.8 ± 40.6 |
| Act.s/cT | 19.5 ± 17.7 | 35.0 ± 34.4 | 59.4 ± 61.0 |
| NK cell | 201 ± 106 | 187 ± 163 | 228 ± 177 |
| Monocyte | 330 ± 142 | 337 ± 188 | 378 ± 234 |
| Lymphocyte | 2100 ± 585 | 2237 ± 707 | 2466 ± 811 |

Mean ± SD

MULTIPLE REGRESSION ANALYSIS OF MONOCYTES AND EACH PERIPHERAL LYMPHOCYTE SUBPOPULATION

In the same manner as in Example 1, the multiple regression analysis was performed for each group (i.e. the normal control, recurrent, and not-recurrent groups), using Act.s/c T as dependent variable and monocytes and subpopulations, as independent variables to determine whether the multiple regression equation was established or not. The significance of differences in the partial regression coefficients was assessed by t-test and that of differences in the multiple correlation coefficient, by f-test. Further, the significance of subpopulation-related differences in the simple correlation coefficient was examined by t-test.

Further, as in Example 1, multiple regression analysis where monocytes were used as dependent variable and Th and Act.si/h T as independent variables was performed for the purpose of investigating the ATARM. Furthermore multiple regression analysis where NK cells were used as dependent variable and Tsi and Act.si/h T as independent variables was performed to evaluate the function of NK cells. In addition multiple regression analysis where OKIa1 positive lymphocytes were used as dependent variable and monocytes and NK cells as independent variables was performed for the purpose of investigating cooperation between monocytes and NK cells within or around cancer tissues.

MULTIPLE REGRESSION ANALYSIS WITH Act.s/c T AS DEPENDENT VARIABLE AND OTHER PERIPHERAL LYMPHOCYTE SUBPOPULATIONS AND MONOCYTES AS INDEPENDENT VARIABLES a. Normal Control Group In the matrix of simple correlation coefficient, Act.s/c T was noted to correlate strongly with Act.si/h T ($r=0.807$, $p<0.01$). Further, Leu 11$^+$ (NK cells) was not correlated with any subset and monocytes were related to Th ($r=0.246$) and Act.si/h T ($r=0.344$, $p<0.05$).

The multiple regression equation was significantly established for Act.s/c T ($r=0.92893$, $p<0.01$; constant=0.27972). It was also established significantly in terms of partial regression coefficient with NK cells ($p<0.05$), Tc ($p<0.05$), Ts ($p<0.05$) and Act.si/h T ($p<0.01$). The contributions were 0.83, 0.09, 3.73, 7.71, 65.05, 1.79 and 1.55% for Th, Tsi, Tc, Ts, Act.si/h T, monocytes and NK cells, respectively and the total contribution was 86.29%. The results are shown in Table 9.

b. Recurrent Group

In the matrix of simple correlation coefficient, Act.s/c T was noted to correlate with Act.si/h T ($r=0.886$, $p<0.01$). NK cell was related to Tsi ($r=0.465$, $p<0.05$), Ts ($r=0.502$, $p<0.01$), Act.si/h T ($r=0.586$, $p<0.01$), Act.s/c T ($r=0.590$, $p<0.01$) and monocytes ($r=0.016$). Monocytes were related to Th ($r=0.039$) and Act.si/h T ($r=0.213$).

The multiple regression equation was significantly established for Act.s/c T ($r=0.94152$, $p<0.01$; constant: $-2.74151$). It was also significantly established only with Act.si/h T ($p<0.01$) in terms of partial regression coefficient. The contributions were 2.38, 0, 0.17, 0.22, 78.56, 2.16, and 0.14% for Th, Tsi, Tc, Ts, Act.si/h T, monocytes and NK cells, respectively and the total contribution was 88.63%. These results are shown in Table 10.

TABLE 9

| (n = 40) Independent variables | OKT3 | OKT4 | OKT8 | OKIa1 | NK cell | Th | Tsi | Tc | Ts | Act. si/hT | Act. s/cT | Monocyte | (Dependent variable = Act.s/cT) Partial regression coefficient | Contribution (%) |
|---|---|---|---|---|---|---|---|---|---|---|---|---|---|---|
| OKT3 |  | 0.835** | 0.802** | 0.625** | 0.230 | 0.783** | 0.529** | 0.727** | 0.497** | 0.380* | 0.331* | 0.132 | 0.00649 | 0.10 |
| OKT4 | 0.835** |  | 0.427** | 0.441** | 0.287 | 0.682** | 0.809** | 0.361* | 0.268 | 0.339* | 0.109 | 0.08 | −0.03621* | 4.73 |
| OKT8 | 0.802** | 0.427** |  | 0.683** | 0.221 | 0.593** | 0.129 | 0.837** | 0.661** | 0.348* | 0.473** | 0.240 | −0.02342 | 0.61 |
| OKIa1 | 0.625** | 0.441** | 0.683** |  | 0.182 | 0.449** | 0.242 | 0.512** | 0.597** | 0.472** | 0.460** | 0.309 | 0.00026 | 0.00 |
| NK cell | 0.230 | 0.287 | 0.221 | 0.182 |  | 0.072 | 0.156 | 0.017 | 0.227 | 0.162 | 0.218 | 0.297 | 0.03956* | 1.55 |
| Th | 0.783** | 0.682** | 0.593** | 0.449** | 0.072 |  | 0.346* | 0.543** | 0.271 | 0.418** | 0.317* | 0.246 | 0.01838 | 0.83 |
| Tsi | 0.529** | 0.809** | 0.129 | 0.242 | 0.156 | 0.346* |  | 0.092 | 0.196 | 0.208 | −0.005 | −0.087 | 0.00799 | 0.09 |
| Tc | 0.727** | 0.361* | 0.837** | 0.512** | 0.017 | 0.543** | 0.092 |  | 0.372* | 0.130 | 0.310 | 0.095 | 0.03714* | 3.73 |
| Ts | 0.497** | 0.268 | 0.661** | 0.597** | 0.227 | 0.271 | 0.196 | 0.372* |  | 0.425** | 0.596** | 0.100 | 0.05911* | 7.71 |
| Act. si/hT | 0.380* | 0.339* | 0.348* | 0.472** | 0.162 | 0.418** | 0.208 | 0.130 | 0.425** |  | 0.807** | 0.344* | 0.73339** | 65.05 |
| Act. s/cT | 0.331* | 0.109 | 0.473** | 0.460** | 0.218 | 0.317* | −0.005 | 0.310 | 0.596** | 0.807** |  | 0.204 | — | — |
| Monocyte | 0.132 | 0.080 | 0.240 | 0.309 | 0.297 | 0.246 | −0.087 | 0.095 | 0.100 | 0.344* | 0.204 |  | −0.01738 | 1.79 |
| Constant |  |  |  |  |  |  |  |  |  |  |  |  | 0.27972 | 86.29 (Sum) |

Multiple correlation coefficient = 0.92893 ($p < 0.01$)
*$p < 0.05$
**$p < 0.01$ (t test)

TABLE 10

(n = 27) (Dependent variable = Act.s/cT)

| Independent variables | OKT3 | OKT4 | OKT8 | OKIal | NK cell | Th | Tsi | Tc | Ts | Act. si/hT | Act. s/cT | Mono-cyte | Partial regression coefficient | Contribution (%) |
|---|---|---|---|---|---|---|---|---|---|---|---|---|---|---|
| OKT3 |  | 0.617** | 0.620** | 0.670** | 0.412* | 0.575** | 0.443* | 0.532** | 0.111 | 0.364 | 0.379 | 0.232 | 0.00035 | 0.00 |
| OKT4 | 0.617** |  | 0.342 | 0.335 | 0.640** | 0.471* | 0.583** | 0.235 | 0.350 | 0.617** | 0.547** | 0.276 | −0.00870 | 0.11 |
| OKT8 | 0.620** | 0.342 |  | 0.522** | 0.252 | 0.314 | 0.093 | 0.864** | 0.503** | 0.069 | 0.282 | 0.202 | 0.01227 | 4.89 |
| OKIal | 0.670** | 0.335 | 0.522** |  | 0.099 | 0.240 | 0.241 | 0.595** | −0.114 | −0.013 | 0.090 | −0.013 | 0.00182 | 0.00 |
| NK cell | 0.412* | 0.640** | 0.252 | 0.099 |  | 0.378 | 0.465* | 0.046 | 0.502 | 0.586** | 0.590** | 0.016 | 0.01071 | 0.14 |
| Th | 0.575** | 0.471* | 0.314 | 0.240 | 0.378 |  | 0.187 | 0.182 | 0.116 | 0.368 | 0.269 | 0.039 | −0.02003 | 2.38 |
| Tsi | 0.443* | 0.583** | 0.093 | 0.241 | 0.465* | 0.187 |  | 0.025 | 0.246 | 0.473* | 0.432* | 0.071 | −0.00056 | 0.00 |
| Tc | 0.532** | 0.235 | 0.864** | 0.595** | 0.046 | 0.182 | 0.025 |  | 0.155 | −0.076 | 0.117 | 0.322 | 0.02063 | 0.17 |
| Ts | 0.111 | 0.350 | 0.503** | −0.114 | 0.502** | 0.116 | 0.246 | 0.155 |  | 0.344 | 0.501** | −0.113 | 0.04733 | 0.22 |
| Act.si/hT | 0.364 | 0.617** | 0.069 | −0.013 | 0.586** | 0.368 | 0.473* | −0.076 | 0.344 |  | 0.886** | 0.213 | 0.85532** | 78.56 |
| Act.s/cT | 0.379 | 0.547** | 0.282 | 0.090 | 0.590** | 0.269 | 0.432* | 0.117 | 0.501** | 0.866* |  | 0.090 | — | — |
| Monocyte | 0.232 | 0.276 | 0.202 | −0.013 | 0.016 | 0.039 | 0.071 | 0.322 | −0.113 | 0.213 | 0.090 |  | −0.02807 | 2.16 |
| Constant |  |  |  |  |  |  |  |  |  |  |  |  | −2.74151 | 88.63 (Sum) |

Multiple correlation coefficient = 0.94152 ($p < 0.01$)

*$p < 0.05$
**$p < 0.01$ (t test)

c. Not-Recurrent Group

In the matrix of simple correlation coefficient, Act.s/c T was noted to correlate with Act.si/h T (r=0.754, p<0.01) and NK cell was related to Tsi (r=0.046), Ts (r=0.152), Act.si/h T (r=0.195) and monocytes (r=−0.071). Monocytes were related to Th (r=0.485, p<0.01) and Act.si/h T (r=−0.069).

The multiple regression equation was significantly established for Act.s/c T (r=0.87106, p<0.01; constant: 0.84916). It was significantly established only with Act.si/h T (p<0.01) in terms of partial regression coefficient. The contributions were 1.5, 6.22, 3.87, 6.67, 56.81, 0.18, and 0.02% for Th, Tsi, Tc, Ts, Act.si/h T, monocytes and NK cells, respectively and the total contribution was 75.87%. These results are shown in Table 11.

MULTIPLE REGRESSION ANALYSIS WITH MONOCYTE AS DEPENDENT VARIABLE AND Act.si/h T AND Th AS INDEPENDENT VARIABLES a. Normal Control Group

Monocytes were related to Act.si/h T (r=0.34396, p<0.05) and the equation of relation was established with such cells alone. This suggested that the ATARM from monocytes to Mφ and to Act. Th was established. Further, a correlation coefficient (r) of about 0.34396 in normal persons may be used as a standard for evaluation in group comparison in the future.

TABLE 11

(n = 32) (Dependent variable = Act.s/cT)

| Independent variables | OKT3 | OKT4 | OKT8 | OKal | NK cell | Th | Tsi | Tc | Ts | Act. si/hT | Act. s/cT | Mono-cyte | Partial regression coefficient | Contribution (%) |
|---|---|---|---|---|---|---|---|---|---|---|---|---|---|---|
| OKT3 |  | 0.858** | 0.854** | 0.635** | −0.063 | 0.700** | 0.621** | 0.857** | 0.022 | 0.021 | −0.055 | 0.497** | 0.02418 | 0.17 |
| OKT4 | 0.858** |  | 0.543** | 0.450** | −0.068 | 0.797** | 0.735** | 0.536** | −0.107 | 0.126 | −0.140 | 0.441* | 0.05282 | 0.06 |
| OKT8 | 0.854** | 0.543** |  | 0.702** | −0.056 | 0.468** | 0.318 | 0.937** | 0.064 | −1.123 | 0.020 | 0.573** | 0.04617 | 0.19 |
| OKIal | 0.635** | 0.450** | 0.702** |  | 0.355* | 0.371* | 0.308 | 0.627** | −0.013 | −0.059 | −0.058 | 0.420* | −0.01453 | 0.18 |
| NK cell | −0.063 | −0.068 | −0.056 | 0.355* |  | −0.076 | 0.046 | −0.111 | 0.152 | 0.195 | 0.124 | −0.071 | 0.00658 | 0.02 |
| Th | 0.700** | 0.797** | 0.468** | 0.371* | −0.076 |  | 0.301 | 0.431* | −0.166 | 0.299 | 0.054 | 0.485** | −0.06938 | 1.50 |
| Tsi | 0.621** | 0.735** | 0.318 | 0.308 | 0.046 | 0.301 |  | 0.359* | 0.187 | 0.081 | −0.187 | −0.053 | −0.12426 | 6.22 |
| Tc | 0.857** | 0.536** | 0.937** | 0.627** | −0.111 | 0.431* | 0.359* |  | 0.069 | −0.154 | 0.001 | 0.457** | 0.04564 | 3.87 |
| Ts | 0.022 | −0.107 | 0.064 | −0.013 | 0.152 | −0.166 | 0.187 | 0.069 |  | 0.557** | 0.596** | −0.260 | 0.10824 | 6.67 |
| Act.si/hT | 0.21 | 0.126 | −0.123 | −0.059 | 0.195 | 0.299 | 0.081 | −0.154 | 0.557** |  | 0.754** | −0.069 | 1.22341** | 56.81 |
| Act.s/cT | −0.055 | −0.140 | 0.020 | −0.058 | 0.124 | 0.054 | −0.187 | 0.001 | 0.596** | 0.754** |  | −0.034 | — | — |
| Monocyte | 0.497** | 0.441* | 0.573** | 0.420* | −0.071 | 0.485** | −0.053 | 0.457** | −0.260 | −0.069 | −0.034 |  | −0.02212 | 0.18 |
| Constant |  |  |  |  |  |  |  |  |  |  |  |  | 0.84196 | 75.87 (Sum) |

Multiple correlation coefficient = 0.87106 ($p < 0.01$)

*$p < 0.05$
**$p < 0.01$ (t test)

b. Recurrent Group

The multiple regression equation was not established between monocytes on the one hand and Th and Act.si/h T on the other (r=0.32754). In particular, the contribution rate of Act.si/h T was lower (4.55%) than in the normal control group (11.83%). It was indicated by this finding that the relationship between monocytes and helper-series T lymphocytes was extremely impaired. Since no significance was noted, it was considered completely impaired.

c. Not-Recurrent Group

In the not-recurrent group, the multiple regression equation was significantly established (r=0.53491, p<0.01) and recovery of function between monocytes and helper-series T lymphocytes was indicated. However, since Th as precursor cells accounted for the greater part in contribution and the value of partial regression coefficient for Act.si/h T was negative, predominance of Act.Tsi rather than Act. Th was suggested. Thus, it was suggested that the relationship between monocytes and helper-series T lymphocytes had not yet functioned normally. These results are shown in Table 12.

c. Not-Recurrent Group

In the not-recurrent group, the multiple regression equation was not established and the function of NK cells was found almost the same as in the normal control group.

These results are shown in Table 13.

TABLE 12

| Dependent variable = | Normal control group (n = 40) | | Recurrent group (n = 27) | | Not-recurrent group (n = 32) | |
|---|---|---|---|---|---|---|
| Monocyte Independent variables | Partial regression coefficient | Contribution (%) | Partial regression coefficient | Contribution (%) | Partial regression coefficient | Contribution (%) |
| Th | — | — | −0.03609 | 0.18 | 0.52569** | 23.56 |
| Act.si/hT | 2.4962* | 11.83 | 1.11382 | 4.55 | −1.35543 | 5.05 |
| Constant | 263.222 | Sum 11.83 | 303.305 | Sum 4.73 | 197.47 | Sum 28.61 |
| Multiple correlation coefficient | = 0.34396(p < 0.01) | | = 0.21754(n.s.) | | = 0.53491(p < 0.01) | | n.s.: not significant
*p < 0.05
**p < 0.01 (t test)

MULTIPLE REGRESSION ANALYSIS WITH NK CELL AS DEPENDENT VARIABLE AND Act.si/h T AND Tsi AS DEPENDENT VARIABLES a. Normal Control Group

The multiple regression equation was not established with NK cell and it was suggested that these cells were not activated functionally.

b. Recurrent Group

In the recurrent group, the equation of relation was established only with Act.si/h T (r=0.58626, p<0.01) and it was shown that NK cells were activated functionally.

TABLE 13

| Dependent variable = | Normal control group (n = 40) | | Recurrent group (n = 27) | | Not-recurrent group (n = 32) | |
|---|---|---|---|---|---|---|
| NK cell Independent variables | Partial regression coefficient | Contribution (%) | Partial regression coefficient | Contribution (%) | Partial regression coefficient | Contribution (%) |
| Tsi | 0.08025 | 1.58 | — | — | 0.02445 | 0.09 |
| Act.si/hT | 0.73532 | 2.62 | 2.45356** | 34.37 | 0.83908 | 3.81 |
| Constant | 149.825 | Sum 4.20 | 72.6671 | Sum 34.37 | 174.908 | Sum 3.90 |
| Multiple correlation coefficient | = 0.20490(n.s.) | | = 0.58626(p < 0.01) | | = 0.19737(n.s.) | | n.s.: not significant
*p < 0.05
**p < 0.01 (t test)

MULTIPLE REGRESSION ANALYSIS WITH OKIa1 POSITIVE LYMPHOCYTE AS DEPENDENT VARIABLE AND MONOCYTE AND NK CELL AS INDEPENDENT VARIABLES a. Normal Control Group

In the normal control group, no significance was noted (r=0.32308) and the multiple regression equation was not established.

Since it was unnecessary in normal persons that OKIa1 antigen is developed to activate lymphocytes or monocytes, the contributions of monocytes and NK cell were increased. The results suggested that their functions were activated. In particular, it was shown by the positive values of partial regression coefficient for both subsets that the normal cooperative relationship was maintained immunologically and activated Mφ was predominant. These results are shown in Table 14.

TABLE 14

| Dependent variable = | Normal control group (n = 40) | | Recurrent group (n = 27) | | Not-recurrent group (n = 32) | |
|---|---|---|---|---|---|---|
| OKIa1 Independent variables | Partial regression coefficient | Contribution (%) | Partial regression coefficient | Contribution (%) | Partial regression coefficient | Contribution (%) |
| Monocyte | 0.61131 | 9.54 | −0.01627 | 0.97 | 0.72737** | 17.64 |
| NK cell | 0.289 | 0.89 | 0.12556 | 0.02 | 0.83061* | 14.88 |
| Constant | 328.051 | Sum 10.43 | 452.36 | Sum 0.99 | 79.5165 | Sum 32.52 |
| Multiple correlation coefficient | = 0.32308(n.s.) | | = 0.09982(n.s.) | | = 0.57028 (p < 0.01) | | n.s. = not significant
*p < 0.05
**p < 0.01 (t test)

the contributions of 9.54 and 0.89% for monocytes and NK cell, respectively, were considered to represent normal conditions undergoing neither immunological enhancement nor suppression.

b. Recurrent Group

In the recurrent groups, the multiple regression equation was not established (r=0.09982) and the contributions of monocytes and NK cells were extremely decreased. These results suggested hypofunction of both cells. In particular, the negative partial regression coefficient for monocytes suggested predominance of suppressor Mφ.

c. Not-Recurrent Group

In the not-recurrent group, the multiple regression equation was significantly established (r=0.57028, p<0.01) and It was confirmed by the foregoing results in the normal control group that the immunity promoting series based on the ATARM from monocyte to Mφ and to Act.Th was almost balanced with the immunosuppressive series from Act. Tsi to Act.Ts, that Act.Tc maintained its function and also that the function of NK cells was neither potentiated nor suppressive on Act.Tsi.

In the recurrent group, the ATARM from monocyte to Act. Th was completely impaired. NK cells were found to exert a significant suppressive action on Act.Tsi.

In the not-recurrent group, suppressive lymphocytes were predominant as compared with the normal control group, and the ATARM from monocyte to Act.Th was still impaired. A strong relationship was noted between helper T lymphocyte and monocyte but an inverse correlation between activated helper T lymphocyte and monocyte. This explains no significant suppressive function of NK cell on Act.Tsi.

Thus, as in Example 1, it is possible to estimate to which one of the groups (i.e. the normal control, recurrent and not-recurrent groups) the result of measurement with a patient under therapy belongs, and to determine whether the treatment is appropriates or not.

For the purpose of more detailed decision-making of treatment, cellular immunokinematograms should be drawn as follows.

CELLULAR IMMUNOKINEMATOGRAM

In drawing cellular immunokinematograms, the contributions obtained as a result of the multiple regression analysis were arranged on the basis of the mutual relationship between different subsets, in the same manner as in Example 1. The cellular immunokinematograms thus obtained are shown in FIGS. 2A–2C.

From these immunokinematograms can be shown the following:

In the recurrent group, helper- and suppressor-series T lymphocytes were seemingly well-balanced with each other to maintain the function of Act.Tc. However, the process from monocytes to Act.Th was impaired completely.

In the not-recurrent group, suppressor-series T lymphocytes were predominant. In the process from monocytes to Act.Th, however, suppressive Mφ was predominant and its suppressive function was confirmed to be potentiated.

Example 3

(1) The counts of each peripheral lymphocyte subpopulation and monocyte obtained in Example 1 were used to perform the above-mentioned multiple regression analyses (MRAs) (A)–(E), namely "the immunologic three-factor sets", i.e. MRAs with monocyte as dependent variable and Act.si/h T and Th as independent variables, with NK cell as dependent variable and Act.si/h T and Tsi as independent variables and with OKIa1 positive lymphocyte as dependent variable and monocyte and NK cell as independent variables, respectively, whereby the standardized partial regression coefficients (SPRCs) and the multiple correlation coefficients (MCCs) in the respective groups were determined. These results are shown in Table 15 and FIG. 6(B).

(2) Secondly, the MRAs (A)–(C) were carried out as in (1) above, using the data of peripheral lymphocyte and monocyte counts obtained in Example 2. These results are shown in Table 16.

Furthermore, in FIG. 3, the numerical values for (A) to (C) shown in Table 15 were separately plotted in respect of the normal control, progressive disease and stable or improved disease groups, respectively. The respective MCCs are shown therein with the numerical values written in. FIG. 6(A) is a three-dimensional representation of FIG. 3 where the MCCs in FIG. 3 are plotted along the hight (Z-axis). FIG. 4 is a graph obtained by representing the numerical values in Table 16 as described for FIG. 3.

The numerical values shown in Table 15, namely the SPRC of each independent variable and the corresponding MCC obtained by the MRA(C) with OKIa1 positive cell as dependent variable and monocyte and NK cell as independent variables, can be converted into the coordinate points on the three-dimensional graph by plotting the respective SPRCs along X and Y axes, respectively, and the MCCs along Z axis. Likewise, the coordinate points of Act.T and Act.B obtained by MRAs(D) and (E) with Act.T and Act.B, respectively, as dependent variables and monocyte and NK cell as independent variables, can be plotted for solid representation. These results are shown in FIGS. 6B–6D and the right of FIG. 7. In this way, the coordinate point obtained by (C) can be separated into the coordinate points obtained by (D) and (C).

TABLE 15

|  | Normal control group (n = 40) | Progressive disease group (n = 50) | Stable or improved group (n = 93) |
| --- | --- | --- | --- |
| A |  |  |  |
| Act.si/hT* | 0.123497 | 0.357 | 0.288939 |
| Multiple correlation coefficient | 0.292302 | 0.025331 | −0.028511 |
|  | 0.361784 | 0.363762 | 0.284602 |
| B |  |  |  |
| Tsi* | 0.128355 | 0.130975 | −0.108097 |
| Act.si/hT* | 0.135293 | 0.469714 | 0.397981 |
| Multiple correlation coefficient | 0.204903 | 0.522209 | 0.413896 |
| C |  |  |  |
| NK cell* | 0.098971 | 0.150721 | 0.430453 |
| Monocyte* | 0.279533 | 0.362853 | 0.197735 |
| Multiple correlation coefficient | 0.323077 | 0.430755 | 0.490599 |
| NK cell* | 0.122544 | 0.635762 | 0.545705 |
| Monocyte* | 0.25562 | −0.151983 | −0.050313 |
| Multiple correlation coefficient | 0.314612 | 0.6101101 | 0.543195 |
| E |  |  |  |
| NK cell* | 0.089538 | 0.084333 | 0.330131 |
| Monocyte* | 0.263762 | 0.384272 | 0.215153 |
| Multiple correlation coefficient | 0.302697 | 0.416229 | 0.410947 |

*Standardized partial regression coefficient

TABLE 16

|  | Normal control group (n = 40) | Recurrent group (n = 27) | Not-recurrent group (n = 32) |
| --- | --- | --- | --- |
| A |  |  |  |
| Th* | 0.123497 | −0.045375 | 0.555845 |
| Act.si/hT* | 0.292302 | 0.230123 | −0.235544 |
| Multiple correlation coefficient | 0.361784 | 0.21754 | 0.534908 |
| B |  |  |  |
| Tsi* | 0.128355 | 0.241964 | 0.029923 |
| Act.si/hT* | 0.135293 | 0.471792 | 0.192667 |
| Multiple correlation coefficient | 0.204903 | 0.623815 | 0.197369 |
| C |  |  |  |
| NK cell* | 0.098971 | 0.098957 | 0.386759 |
| Monocyte* | 0.279533 | −0.014827 | 0.447517 |
| Multiple correlation coefficient | 0.323077 | 0.099820 | 0.570277 |

*Standardized partial regression coefficient

Example 4

For treatments 1–3 in the following case, the standardized partial regression coefficients for immunologic three-factor sets, the partial regression coefficients, the contributions and the multiple correlation coefficients were determined and then the immunokinetics were evaluated.

[A case report of 59 year-old male with bladder cancer]

On Jun. 4, 1987, he was diagnosed as multiple superficial bladder cancer and underwent transurethral resection of bladder tumor (TUR-Bt) and random biopsy. Transitional cell carcinoma with the category of stage pT1b and grade 2 of malignancy was observed, as well as multiple carcinoma in situ in all of ten biopsied specimens.

(Treatment 1)

For the prevention of recurrence, instillation into the urinary bladder of 9 Mega-Unit (MU) of gamma-interferon was initiated one week after the TUR-Bt operation, once a week for the first four weeks and once a month thereafter. But the postoperative urinary cytology became positive 4 months after the operation and he underwent TUR-biopsy of the bladder on November 6, with the result that the recurrence of multiple carcinoma in situ was noted.

On Jan. 29, 1988, a catheter for arterial infusion was settled for the subselective arterial infusion therapy, puncturing the left femoral artery. The five-drug combination chemotherapy (COMPA) consisting of cisplatin, vincristine (trademark: Oncovin), methotrexate, peplomycin and adriamycin was carried out in 3 courses and he obtained a complete response.

(Treatment 2)

From Mar. 15, 1988, after the completion of arterial infusion therapy, the combination of 9 MU of gamma-interferon (IFN-γ) and 200 mcg of muramyl dipeptide (MDP; synthetic product corresponding to the cell wall skeleton of tubercle bacillus) was instilled into the cavity of the urinary bladder. The interval of instillation was the same as that for the single agent instillation of IFN-γ. From about October, 1988, however, the urinary cytology became positive again and carcinoma in situ recurred.

(Treatment 3)

From Dec. 5, 1988, the combined therapy by subcutaneous injection of 200 mcg of MDP for general sensitization (priming) and instillation into the urinary bladder of 9 MU of IFN-γ, 6 MU of IFN-α and 200 mcg of MDP (eliciting) was carried out for the purpose of treatment. The peroral administration of 100 mg/day of cyclophosphamide (trademark: Endoxan) was simultaneously given twice per day (morning and evening) for 2 weeks and repeated every 4 weeks. The priming and the eliciting were carried out once per week (a total of 4 times), twice per two weeks (a total of 8 times) and once per month (a total of nine times). As of the end of August, 1989, the urinary cytology continued to be negative and no evidence to show cancer was noted by cystoscopy, different examinations such as ultrasound and CT-scanning, thus indicating a satisfactory progress.

[The assessment of immunokinetics]

In the same manner as in Example 3, the values for the immunologic three-factor sets were determined in the normal control group and each of treatments 1–3 mentioned above.

The results of lymphocyte subpopulations and monocyte counts for normal controls are shown in Table 17, those of multiple regression analysis of (A) in Table 18, those of multiple regression analysis of (B) in Table 19 and the those of multiple regression analysis of (C) in Table 20.

The results for treatments 1–3 are also shown in the same order as for the normal controls. Thus the results for treatment 1 are shown in Tables 21 to 24, those for treatment 2 in Tables 25 to 28 and those for treatment 3 in Tables 29 to 32.

TABLE 17

| (n = 40) | Unit:/mm³ |
|---|---|
| Th | 423 ± 155 |
| Tsi | 387 ± 170 |
| Act.si/hT | 25.8 ± 19.5 |
| NK Cell | 201 ± 106 |
| Monocyte | 330 ± 142 |
| OKIaI | 588 ± 310 |

Mean ± SD

TABLE 18

Dependent variable = Monocyte (n = 40)

| Independent variables | Standardized partial regression coefficient | Partial regression coefficient | Contribution (%) |
|---|---|---|---|
| Th | 0.123497 | 0.11272 | 1.26 |
| Act.si/hT | 0.292302 | 2.1213 | 11.83 |
| Constant | | 225.542 | 13.09 Sum |

Multiple correlation coefficient = 0.361784 (n.s.)

n.s.: not significant (f test)

TABLE 19

Dependent variable = NK cell (n = 40)

| Independent variables | Standardized partial regression coefficient | Partial regression coefficient | Contribution (%) |
|---|---|---|---|
| Tsi | 0.128355 | 0.0802545 | 1.58 |
| Act.si/hT | 0.135293 | 0.735321 | 2.62 |
| Constant | | 149.825 | 4.20 Sum |

Multiple correlation coefficient = 0.204903 (n.s.)

n.s.: not significant (f test)

TABLE 20

Dependent variable = OKIaI (n = 40)

| Independent variables | Standardized partial regression coefficient | Partial regression coefficient | Contribution (%) |
|---|---|---|---|
| NK cell | 0.0989708 | 0.289003 | 0.89 |
| Monocyte | 0.279533 | 0.611309 | 9.54 |
| Constant | | 328.051 | 10.43 Sum |

Multiple correlation coefficient = 0.323077 (n.s.)

n.s.: not significant (f test)

TABLE 21

| (n = 7) | Unit:/mm³ |
|---|---|
| Th | 574 ± 119 |
| Tsi | 651 ± 253 |
| Act.si/hT | 45.9 ± 22.2 |
| NK Cell | 237 ± 177 |

TABLE 21-continued

| (n = 7) | Unit:/mm³ |
|---|---|
| Monocyte | 514 ± 334 |
| OKIal | 807 ± 322 |

Mean ± SD

TABLE 22

Dependent variable = Monocyte (n = 7)

| Independent variables | Standardized partial regression coefficient | Partial regression coefficient | Contribution (%) |
|---|---|---|---|
| Th | 0.133871 | 0.376401 | 1.74 |
| Act.si/hT | −0.206615 | −3.11349 | 3.39 |
| Constant | | 440.99 | Sum 5.13 |

Mutliple correlation coefficient = 0.226519 (n.s.)

n.s.: not significant (f test)

TABLE 23

Dependent variable = NK cell (n = 7)

| Independent variables | Standardized partial regression coefficient | Partial regression coefficient | Contribution (%) |
|---|---|---|---|
| Tsi | 0.32915 | 0.229814 | 10.29 |
| Act.si/hT | 0.737381 | 5.88337 | 44.05 |
| Constant | | −182.243 | Sum 54.34 |

Multiple correlation coefficient = 0.737155 (n.s.)

n.s.: not significant (f test)

TABLE 24

Dependent variable = OKIal (n = 7)

| Independent variables | Standardized partial regression coefficient | Partial regression coefficient | Contribution (%) |
|---|---|---|---|
| NK cell | −0.394324 | −0.718647 | 15.03 |
| Monocyte | −0.629799 | −0.607734 | 31.09 |
| Constant | | 1290.32 | Sum 46.12 |

Multiple correlation coefficient = 0.679087 (n.s.)

n.s.: not significant (f test)

TABLE 25

| (n = 5) | Unit:/mm³ |
|---|---|
| Th | 468 ± 108 |
| Tsi | 374 ± 172 |
| Act.si/hT | 48.9 ± 18.3 |
| NK Cell | 294 ± 122 |
| Monocyte | 580 ± 259 |
| OKIal | 289 ± 68 |

Mean ± SD

TABLE 26

Dependent variable = Monocyte (n ± 5)

| Independent variables | Standardized partial regression coefficient | Partial regression coefficient | Contribution (%) |
|---|---|---|---|
| Th | −0.937248 | −0.937248 | 14.11 |
| Act.si/hT | 0.0423683 | 0.598427 | 0.15 |
| Constant | | 989.381 | Sum 14.26 |

Multiple correlation coefficient = 0.37768 (n.s.)

n.s.: not significant (f test)

TABLE 27

Dependent variable = NK cell (n = 5)

| Independent variables | Standardized partial regression coefficient | Partial regression coefficient | Contribution (%) |
|---|---|---|---|
| Tsi | 1.15961 | 0.817615 | 59.23 |
| Act.si/hT | −1.43699 | −0.53279* | 32.44 |
| Constant | | 453.975 | Sum 91.67 |

Multiple correlation coefficient = 0.957419 (n.s.)

*$p < 0.05$ (t test)
n.s.: not significant (f test)

TABLE 28

Dependent variable = OKIal (n = 5)

| Independent variables | Standardized partial regression coefficient | Partial regression coefficient | Contribution (%) |
|---|---|---|---|
| NK cell | 0.831561 | 0.462259 | 32.55 |
| Monocyte | 0.42539 | 0.111103 | 11.29 |
| Constant | | 88.5486 | Sum 43.84 |

Multiple correlation coefficient = 0.662119 (n.s.)

n.s.: not significant (f test)

TABLE 29

| (n = 8) | Unit:/mm³ |
|---|---|
| Th | 371 ± 76 |
| Tsi | 405 ± 77 |
| Act.si/hT | 42.4 ± 32.5 |
| NK Cell | 285 ± 112 |
| Monocyte | 405 ± 198 |
| OKal | 477 ± 181 |

Mean ± SD

TABLE 30

Dependent vairable = Monocyte (n = 8)

| Independent variables | Standardized partial regression coefficient | Partial regression coefficient | Contribution (%) |
|---|---|---|---|
| Th | 0.0003 | 0.000784 | 0.00 |
| Act.si/hT | 0.285619 | 1.73822 | 8.16 |
| Constant | | 330.677 | Sum 8.16 |

Mutliple correlation coefficient = 0.285681 (n.s.)

n.s.: not significant (f test)

TABLE 31

Dependent variable = NK cell (n = 8)

| Independent variables | Standardized partial regression coefficient | Partial regression coefficient | Contribution (%) | |
|---|---|---|---|---|
| Tsi | 0.178866 | 0.261182 | | 2.73 |
| Act.si/hT | 0.741462 | 2.55246 | | 45.31 |
| Constant | | 71.4357 | Sum | 48.04 |

Multiple correlation coefficient = 0.693139 (n.s.)

n.s.: not significant (f test)

TABLE 32

Dependent variable = OKa1 (n = 8)

| Independent variables | Standardized partial regression coefficient | Partial regression coefficient | Contribution (%) | |
|---|---|---|---|---|
| NK cell | 0.416353 | 0.676139 | | 22.17 |
| Monocyte | 0.262873 | 0.241476 | | 6.61 |
| Constant | | 186.84 | Sum | 28.78 |

Multiple correlation coefficient = 0.536508 (n.s.)

n.s.: not significant (f test)

Furthermore, in FIG. 5 is shown a graph indicating the change of correlated functions of the three-factor sets obtained with the normal control group and treatments 1–3.

It has been confirmed from the results mentioned above that the approaching of the dispersion, at the initiation of treatment, of the immunologic three-factor sets to the normal control's pattern in the course of immunotherapy is indicative of healing.

Example 5

The results of a total of thirteen measurements carried out every 2 or 3 days in a normal healthy 49 year-old male and the cellular immunokinematograms obtained therefrom are shown in Tables 33 to 42 and FIG. 8, respectively.

In the upper-left of FIG. 8 shows the T cell immunokinematogram. The symbols in FIG. 8 is shown used to mean the following: →: process of differentiation or maturation; ⁕: non-functioning or impaired antigen recognition mechanism; ⇢: no suppressive function of NK cell; ⇾: accelerating or promoting function; ⇠: suppression; ⇒ and ⇾: cytotoxic function; ●: 0.1%≧ of contribution. The values in % described in the lower part of this upper-left figure are for the contribution of activated suppression inducer/helper T cell versus monocyte or NK cell.

The B cell immunokinematogram is shown in the lower-left of FIG. 8. The symbols in the figure are used to mean the following: ⁕: neither accelerating nor promoting; ⇠: suppression; Baso: basophil; Eosi: eosinophil; Seg: neutrophil.

The immunologic three-factor sets are shown in the right of FIG. 8. The symbols in the figure are used to mean the following: △: the correlation of monocyte versus helper and activated suppression inducer/helper T cells; □: the correlation of NK cell versus suppression inducer and activated suppression inducer/helper T cells; ●: the correlation of OKIa1 positive (activated) lymphocyte versus monocyte and NK cell; ○: the correlation of activated T lymphocyte versus monocyte and NK cell; ◉: the correlation of activated B lymphocyte versus monocyte and NK cell. This example is to demonstrate the possibility of drawing specific immunokinematograms peculiar to individuals.

It has now been confirmed with this example that specific immunokinematograms peculiar to individuals can be drawn.

Example 6

Measurements were carried out on three patients with chronic rheumatoid arthritis to draw T and B cell immunokinematograms and a graph of immunologic three-factor sets. The results are shown in Tables 43 to 52 and FIG. 9. One of the cases, a 59 year-old male, is under treatment and has a stable and improved clinical course 4 months later after the onset of disease. The other cases, 77 and 83 year-old females, had undergone treatment for 8 and 10-odd years, respectively, but are no longer under treatment because of the state of disease being stable and improved. The multiple regression analysis was carried out in the respective cases on the data from 3×5 (15 in total) measurements carried out once every week or 2 weeks.

From these results, it was confirmed that the stable or improved state of disease was due to the immune state being well controlled up to a normal healthy level.

Tables 33–52 shown below are as follows:

Table 33. The results of lymphocyte subpopulations, monocyte and granulocytes (basophil, eosinophil and neutrophil) counts in the peripheral blood of the 49 y.o. healthy male (n=13)

Table 34. The results of multiple regression analysis of the data in Table 33, using activated suppressor/cytotoxic T cell as dependent variable Table 35. The multiple regression analysis between monocyte, helper T cell and activated suppression inducer/helper T cell Table 36. The multiple regression analysis between natural killer cell, suppression inducer T cell and activated suppression inducer/helper T cell Table 37. The standardized partial regression coefficients and multiple correlation coefficients for preparing a graph of immunologic three-factor sets Table 38. The results of multiple regression analysis using activated B cell as dependent variable Table 39. The multiple regression analysis between activated B cell, helper T cell and activated suppression inducer/helper T cell Table 40. The multiple regression analysis between basophil, helper T cell and activated suppression inducer/helper T cell Table 41. The multiple regression analysis between eosinophil, helper T cell and activated suppression inducer/helper T cell Table 42. The multiple regression analysis between neutrophil, helper T cell and activated suppression inducer/helper T cell Table 43. The results of lymphocyte subpopulations, monocyte and granulocytes counts in the peripheral blood of the 59 y.o. male with chronic rheumatoid arthritis under treatment, and of the 77 y.o. and 83 y.o. females with it under no treatment, all these three cases having good clinical courses during the measurements Table 44. The results of multiple regression analysis using activated suppressor/cytotoxic T cell as dependent variable Table 45. The multiple regression analysis between monocyte, helper T cell and activated suppression inducer/helper T cell Table 46. The multiple regression analysis between natural killer cell, suppression inducer T cell and activated suppression inducer/helper T cell Table 47. The standardized partial regression coefficients and multiple correlation coefficients for preparing a graph of immunologic three-factor sets Table 48. The results of multiple regression analysis using activated B cell as dependent variable Table 49. The multiple regression analysis between activated B cell, helper T cell and activated suppression inducer/helper T cell Table 50. The multiple regression analysis between basophil, helper T cell and activated suppression inducer/helper T cell Table 51. The multiple regression analysis between eosinophil, helper T cell and activated suppression inducer/helper T cell Table 52. The multiple regression analysis between neutrophil, helper T cell and activated suppression inducer/helper T cell

TABLE 33

| Unit:/mm$^3$ | (n = 13) |
| --- | --- |
| OKT3 | 1867 ± 281 |
| OKT4 | 1084 ± 174 |
| OKT8 | 689 ± 157 |
| OKa1 | 614 ± 184 |
| Th | 263 ± 84 |
| Tsi | 786 ± 133 |
| Tc | 458 ± 82 |
| Ts | 279 ± 117 |
| Act.si/hT | 89.0 ± 24.5 |
| Act.s/cT | 143.5 ± 61.4 |
| NK | 49 ± 17 |
| Monocyte | 130 ± 53 |
| Act.T | 232.5 ± 69.2 |
| Act.B | 381 ± 147 |
| Basophil | 25 ± 21 |
| Eosinophil | 266 ± 86 |
| Neutrophil | 2489 ± 517 |

Mean ± SD

TABLE 34

| Independent variables | Dependent variable Act.s/cT | |
| --- | --- | --- |
| | Partial regression coefficient | Contribution (%) |
| OKT3 | −0.370896* | 5.64 |
| OKT4 | 0.238379 | 0.16 |
| OKT8 | −0.508682 | 12.6 |
| Th | 0.308995 | 4.42 |
| Tsi | −0.025641 | 1.91 |
| Tc | 0.60887 | 4.48 |
| Ts | 1.36588** | 69.07 |
| Act.si/hT | 0.187919 | 0.04 |
| NK cell | 0.376798 | 0.16 |
| Monocyte | −0.216849 | 1.25 |
| | | (Sum) |
| Constant | 199.631 | 99.80 |
| Multiple correlation coefficient | 0.998937 ($p < 0.05$) | |

*$p < 0.05$,
**$p < 0.01$ (t test)

TABLE 35

| Independent variables | Dependent variable Monocyte | |
| --- | --- | --- |
| | Partial regression coefficient | Contribution (%) |
| Th | 0.107463 | 2.97 |
| Act.si/hT | 0.252071 | 1.33 |
| | | (Sum) |
| Constant | 79.2156 | 4.30 |
| Multiple correlation coefficient | 0.207305 (n.s.) | | n.s.: not significant (f test)

TABLE 36

| Independent variables | Dependent variable NK cell | |
| --- | --- | --- |
| | Partial regression coefficient | Contribution (%) |
| Tsi | 0.009091 | 0.20 |
| Act.si/hT | 0.190682 | 11.03 |
| | | (Sum) |
| Constant | 24.4186 | 11.23 |
| Multiple correlation coefficient | 0.33518 (n.s.) | | n.s.: not significant (f test)

TABLE 37

| | Standarized partial regression coefficient |
| --- | --- |
| A | |
| Th | 0.168394 |
| Act.si/ht | 0.115387 |
| Mutliple correlation coefficient | 0.207305 |
| B | |
| Tsi | 0.071702 |
| Act.si/hT | 0.276463 |
| Multiple correlation coefficient | 0.33518 |
| C | |
| NK cell | 0.181317 |
| Monocyte | 0.132155 |
| Multiple correlation coefficient | 0.234756 |
| D | |
| NK cell | 0.435111 |
| Monocyte | 0.162986 |
| Multiple correlation coefficient | 0.479583 |
| E | |
| NK cell | 0.021822 |

TABLE 37-continued

|  | Standarized partial regression coefficient |
|---|---|
| Monocyte | 0.088407 |
| Multiple correlation coefficient | 0.093145 |

TABLE 38

| | Dependent variable Act.B | |
|---|---|---|
| Independent variables | Partial regression coefficient | Contribution (%) |
| Th | −0.227762 | 0.11 |
| Tsi | −0.286855 | 1.55 |
| Tc | 2.18391 | 8.95 |
| Ts | −1.59677 | 8.42 |
| Act.si/hT | 0.869905 | 0.20 |
| Act.s/cT | 2.75868 | 15.66 |
| NK cell | 4.82383 | 2.50 |
| Monocyte | 1.29852 | 5.18 |
| Neutrophil | 0.056596 | 12.51 |
| Basophil | −3.97208 | 3.27 |
| Eosinophil | −0.510105 | 15.85 |
| | | (Sum) |
| Constant | −668.549 | 74.20 |
| Multiple correlation coefficient | 0.861425 (n.s.) | | n.s.: not significant (f test)

TABLE 39

| | Dependent variable Act.B | |
|---|---|---|
| Independent variables | Partial regression coefficient | Contribution (%) |
| Th | 0.11349 | 0.43 |
| Act.si/hT | 0.139013 | 0.05 |
| | | (Sum) |
| Constant | 339.132 | 0.48 |
| Multiple correlation coefficient | 0.069296 (n.s.) | | n.s.: not significant (f test)

TABLE 40

| | Dependent variable Basophil | |
|---|---|---|
| Independent variables | Partial regression coefficient | Contribution (%) |
| Th | 0.067288 | 7.41 |
| Act.si/hT | 0.102045 | 1.41 |
| | | (Sum) |
| Constant | −1.3228 | 8.82 |
| Multiple correlation coefficient | 0.29705 (n.s.) | | n.s.: not significant (f test)

TABLE 41

| | Dependent variable Eosinophil | |
|---|---|---|
| Independent variables | Partial regression coefficient | Contribution (%) |
| Th | −0.040742 | 0.16 |
| Act.si/hT | −0.299355 | 0.75 |
| | | (Sum) |
| Constant | 303.671 | 0.91 |
| Multiple correlation coefficient | 0.095016 (n.s.) | | n.s.: not significant (f test)

TABLE 42

| | Dependent variable Neutrophil | |
|---|---|---|
| Independent variables | Partial regression coefficient | Contribution (%) |
| Th | −1.21932 | 3.93 |
| Act.si/hT | −0.408117 | 0.04 |
| | | (Sum) |
| Constant | 2846.18 | 3.97 |
| Multiple correlation coefficient | 0.199176 (n.s.) | | n.s.: not significant (f test)

TABLE 43

Unit: /mm³

|  | 59 y.o. male (n = 5) | 77 y.o. female (n = 5) | 83 y.o. female (n = 5) | Sum (n = 15) |
|---|---|---|---|---|
| OKT3 | 1412 ± 191 | 1008 ± 214 | 1356 ± 491 | 1259 ± 356 |
| OKT4 | 1008 ± 133 | 642 ± 144 | 1246 ± 448 | 965 ± 367 |
| OKT8 | 544 ± 136 | 440 ± 126 | 196 ± 62 | 393 ± 184 |
| OKIa1 | 510 ± 361 | 534 ± 140 | 258 ± 112 | 434 ± 251 |
| Th | 590 ± 29 | 356 ± 139 | 162 ± 82 | 369 ± 201 |
| Tsi | 372 ± 101 | 252 ± 99 | 988 ± 307 | 537 ± 380 |
| Tc | 280 ± 84 | 292 ± 101 | 86 ± 26 | 219 ± 121 |
| Ts | 292 ± 94 | 154 ± 61 | 120 ± 49 | 189 ± 101 |
| Act.si/hT | 166.8 ± 38.4 | 79.8 ± 15.2 | 54.3 ± 27.5 | 100.3 ± 56.5 |
| Act.s/cT | 246.7 ± 50.4 | 242.3 ± 98.6 | 61.2 ± 20.4 | 183.4 ± 107.8 |
| NK cell | 38 ± 14 | 43 ± 16 | 35 ± 22 | 39 ± 17 |
| Monocyte | 339 ± 196 | 179 ± 106 | 120 ± 66 | 213 ± 157 |
| Act.T | 413.5 ± 68.8 | 322.1 ± 111.6 | 115.5 ± 44.0 | 283.7 ± 148.7 |
| Act.B | 138 ± 269 | 214 ± 160 | 143 ± 76 | 165 ± 176 |
| Basophil | 11 ± 11 | 19 ± 25 | 14 ± 23 | 15 ± 20 |
| Eosinophil | 66 ± 58 | 114 ± 28 | 53 ± 13 | 78 ± 44 |
| Neutrophil | 4123 ± 509 | 3093 ± 448 | 5148 ± 1096 | 4121 ± 1109 |

Mean ± SD

TABLE 44

| Independent variables | Dependent variable Act.s/cT | |
|---|---|---|
|  | Partial regression coefficient | Contribution (%) |
| OKT3 | 0.013271 | 0.00 |
| OKT4 | 0.393968 | 0.68 |
| OKT8 | −0.013259 | 78.52 |
| Th | −0.027523 | 1.11 |
| Tsi | −0.581591 | 2.58 |
| Tc | 0.037913 | 6.87 |
| Ts | 0.643833 | 2.14 |
| Act.si/hT | −1.50839* | 3.87 |
| NK cell | 0.960777 | 1.10 |
| Monocyte | −0.069336 | 0.24 |
|  |  | (Sum) |
| Constant | 113.464 | 97.06 |
| Multiple correlation coefficient | 0.985225 ($p < 0.05$) | |

*$p < 0.05$ (t test)

TABLE 45

| Independent variables | Dependent variable Monocyte | |
|---|---|---|
|  | Partial regression coefficient | Contribution (%) |
| Th | 0.590448 | 32.73 |
| Act.si/hT | −0.5998 | 1.18 |
|  |  | (Sum) |
| Constant | 54.820 | 33.91 |
| Multiple correlation coefficient | 0.582243 (n.s.) | | n.s.: not significant (f test)

TABLE 46

| Independent variables | Dependent variable NK cell | |
|---|---|---|
|  | Partial regression coefficient | Contribution (%) |
| Tsi | 0.011200 | 5.50 |
| Act.si/hT | 0.130613 | 11.92 |
|  |  | (Sum) |
| Constant | 19.4799 | 17.42 |
| Multiple correlation coefficient | 0.417328 (n.s.) | | n.s.: not significant (f test)

TABLE 47

|  | Standardized partial regression coefficient |
|---|---|
| A | |
| Th | 0.759351 |
| Act.si/ht | −0.216429 |
| Multiple correlation coefficient | 0.582243 |
| B | |
| Tsi | 0.251576 |
| Act.si/hT | 0.43663 |
| Multiple correlation coefficient | 0.417328 |
| C | |
| NK cell | 0.445037 |
| Monocyte | 0.478064 |
| Multiple correlation coefficient | 0.602544 |
| D | |
| NK cell | 0.461599 |

TABLE 47-continued

|  | Standardized partial regression coefficient |
| --- | --- |
| Monocyte | 0.507469 |
| Multiple correlation coefficient | 0.632957* |
| E |  |
| NK cell | 0.289039 |
| Monocyte | 0.282588 |
| Multiple correlation coefficient | 0.372834 |

*$p < 0.05$ (f test)

TABLE 48

| Independent variables | Dependent variable Act.B | |
| --- | --- | --- |
|  | Partial regression coefficient | Contribution (%) |
| Th | −1.2468 | 11.21 |
| Tsi | 0.,060024 | 0.13 |
| Tc | 0.056351 | 0.01 |
| Ts | 1.30477 | 20.60 |
| Act.si/hT | 0.183446 | 0.06 |
| Act.s/cT | 0.784022 | 3.00 |
| NK cell | 0.937972 | 5.30 |
| Monocyte | 0.956598 | 14.43 |
| Neutrophil | 0.081444 | 23.64 |
| Basophil | −1.16985 | 0.74 |
| Eosinophil | 4.65044 | 11.82 |
|  |  | (Sum) |
| Constant | −747.59 | 90.94 |
| Multiple correlation coefficient | 0.953595 (n.s.) | | n.s.: not significant (f test)

TABLE 49

| Independent variables | Dependent variable Act.B | |
| --- | --- | --- |
|  | Partial regression coefficient | Contribution (%) |
| Th | −0.327244 | 3.52 |
| Act.si/hT | 1.28033 | 0.76 |
|  |  | (Sum) |
| Constant | 157.501 | 4.28 |
| Multiple correlation coefficient | 0.206793 (n.s.) | | n.s.: not significant (f test)

TABLE 50

| Independent variables | Dependent variable Basophil | |
| --- | --- | --- |
|  | Partial regression coefficient | Contribution (%) |
| Th | −0.031931 | 3.81 |
| Act.si/hT | 0.052967 | 0.58 |
|  |  | (Sum) |
| Constant | 21.2798 | 4.39 |
| Multiple correlation coefficient | 0.209473 (n.s.) | | n.s.: not significant (f test)

TABLE 51

| Independent variables | Dependent variable Eosinophil | |
| --- | --- | --- |
|  | Partial regression coefficient | Contribution (%) |
| Th | −0.002991 | 0.01 |
| Act.si/hT | 0.013110 | 0.00 |
|  |  | (Sum) |
| Constant | 77.6568 | 0.01 |
| Multiple correlation coefficient | 0.008404 (n.s.) | | n.s.: not significant (f test)

TABLE 52

| Independent variables | Dependent variable Neutrophil | |
| --- | --- | --- |
|  | Partial regression coefficient | Contribution (%) |
| Th | −5.00489 | 7.38 |
| Act.si/hT | 14.4518 | 13.61 |
|  |  | (Sum) |
| Constant | 4520.23 | 20.99 |
| Multiple correlation coefficient | 0.458165 (n.s.) | | n.s: not significant (f test)

Figure 1A:
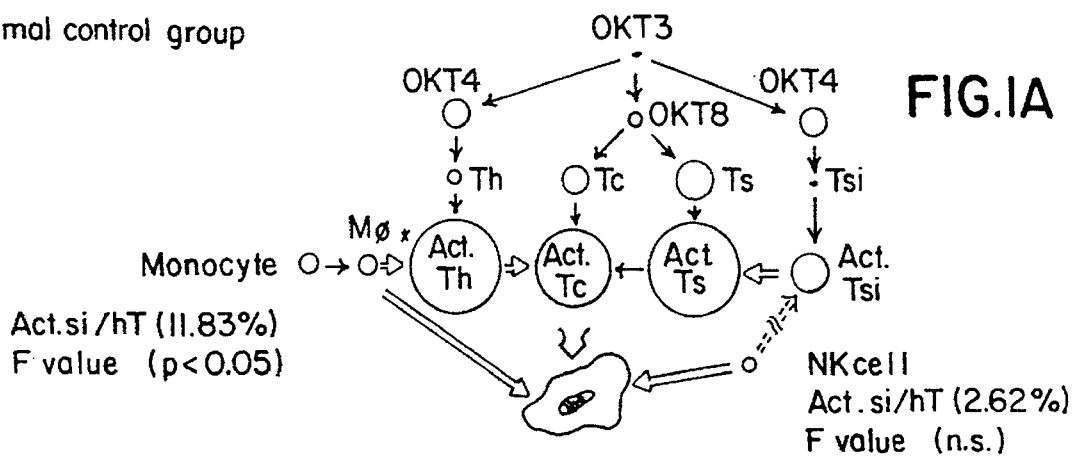
FIG. 1. The cellular immunokinematograms obtained in Example 1
Figure 1B:
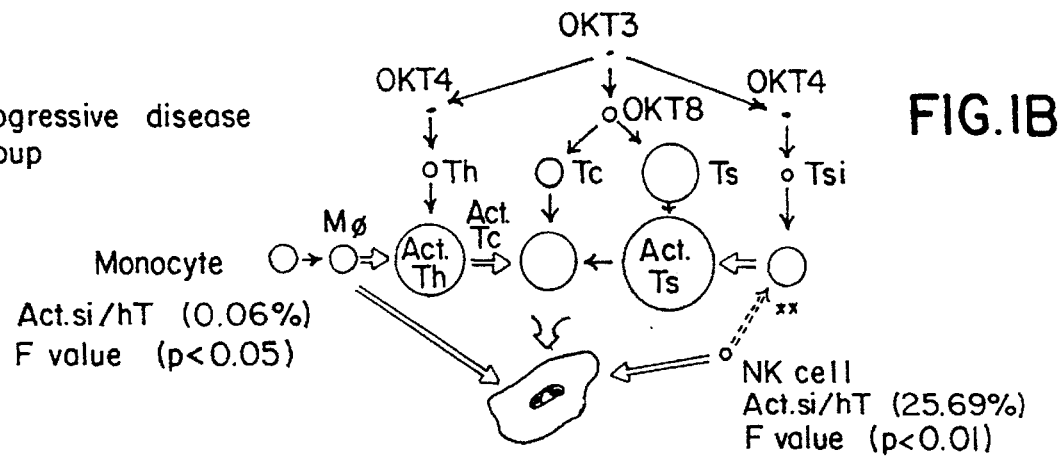
Figure 1C:
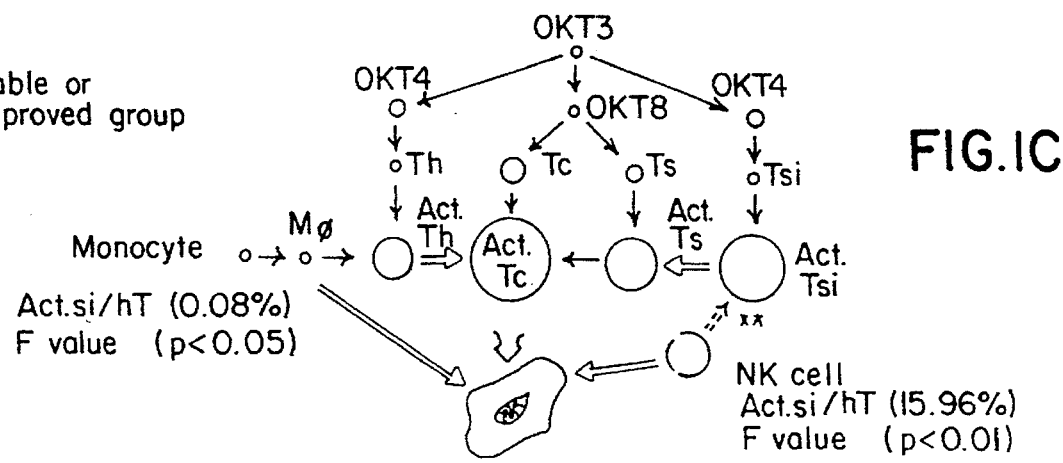
Figure 2A:
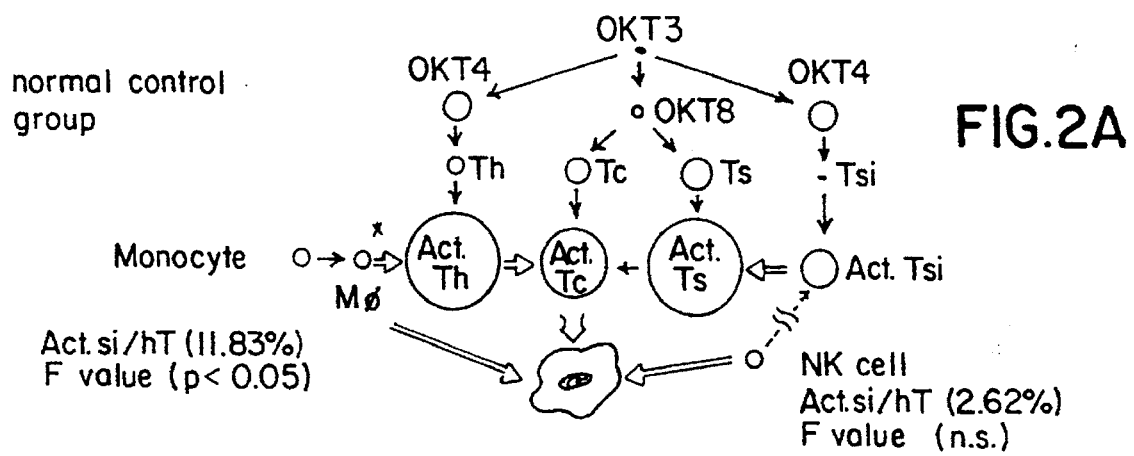
FIG. 2. The cellular immunokinematograms obtained in Example 2
Figure 2B:
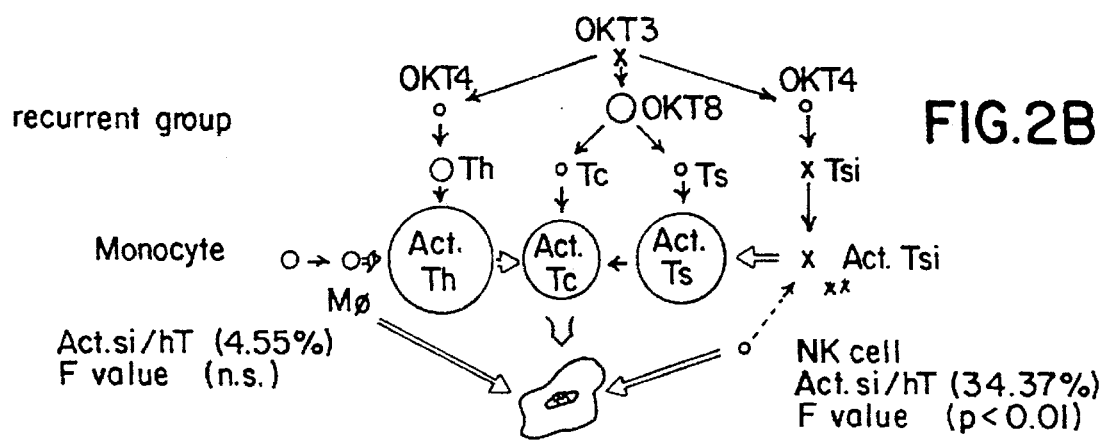
Figure 2C:
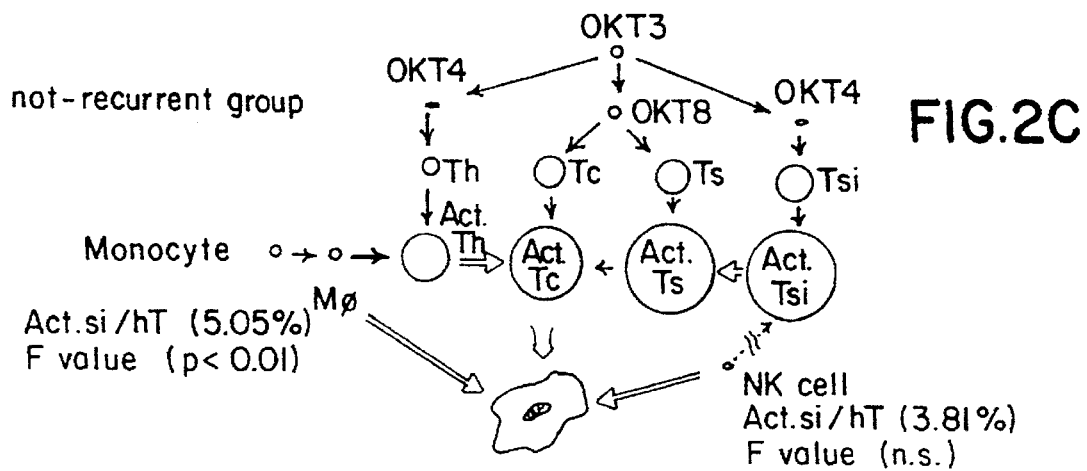
Figure 3:
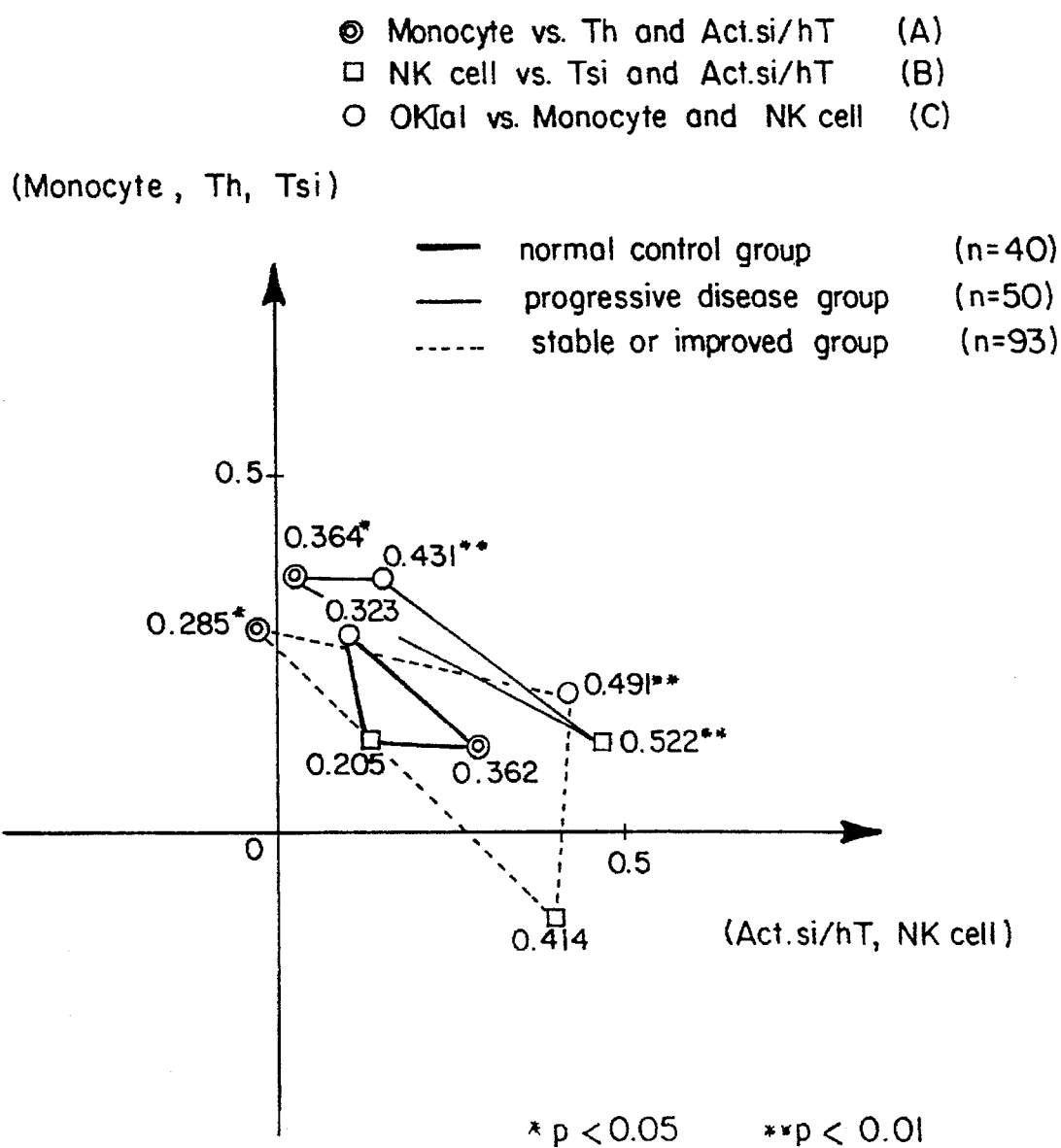
FIG. 3. The correlated graphs of immunologic three-factor sets obtained from Example 1 in accordance with Example 3
Figure 4:
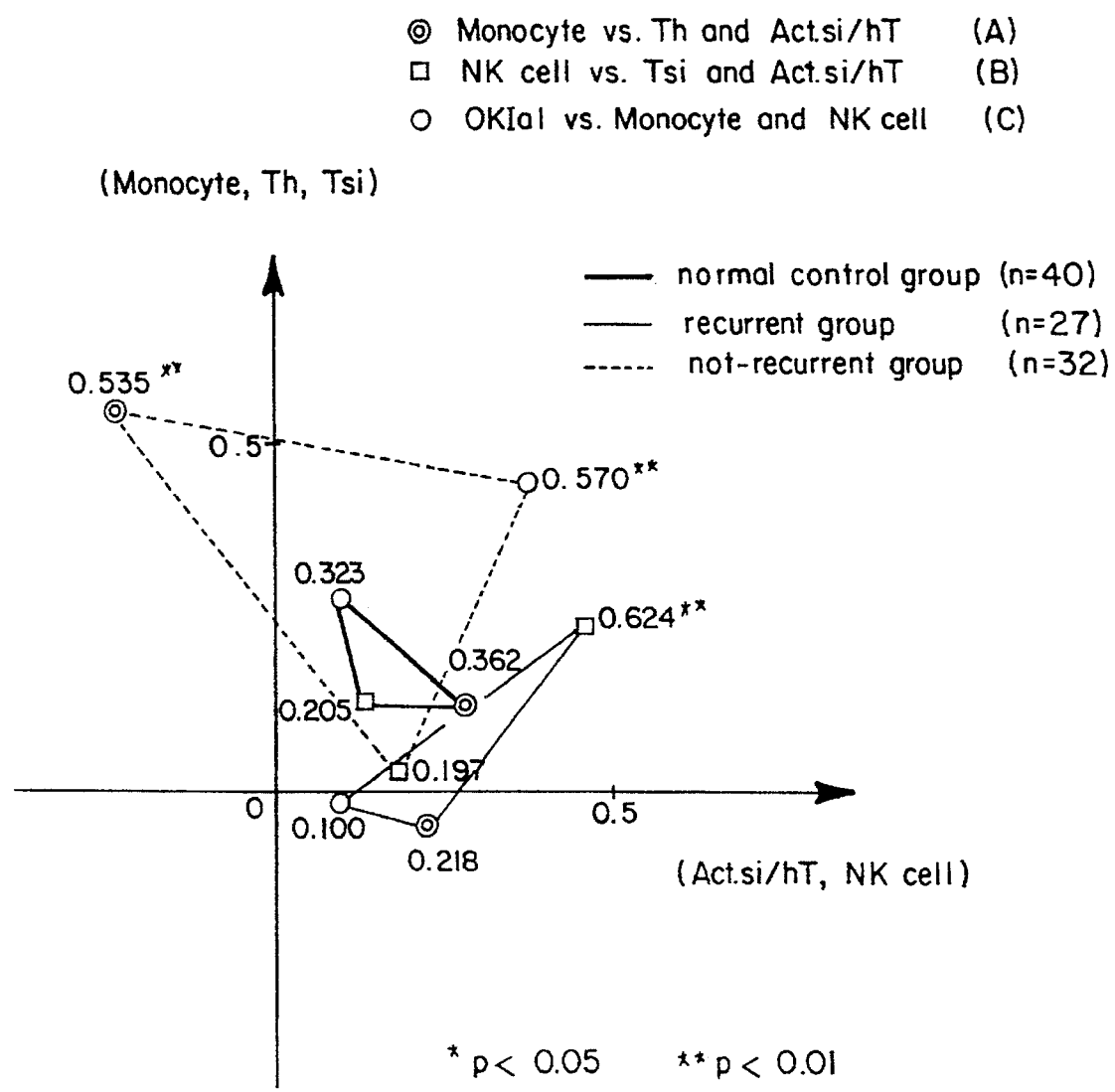
FIG. 4. The correlated graphs of immunologic three-factor sets obtained from Example 2 in accordance with Example 3
Figure 5:
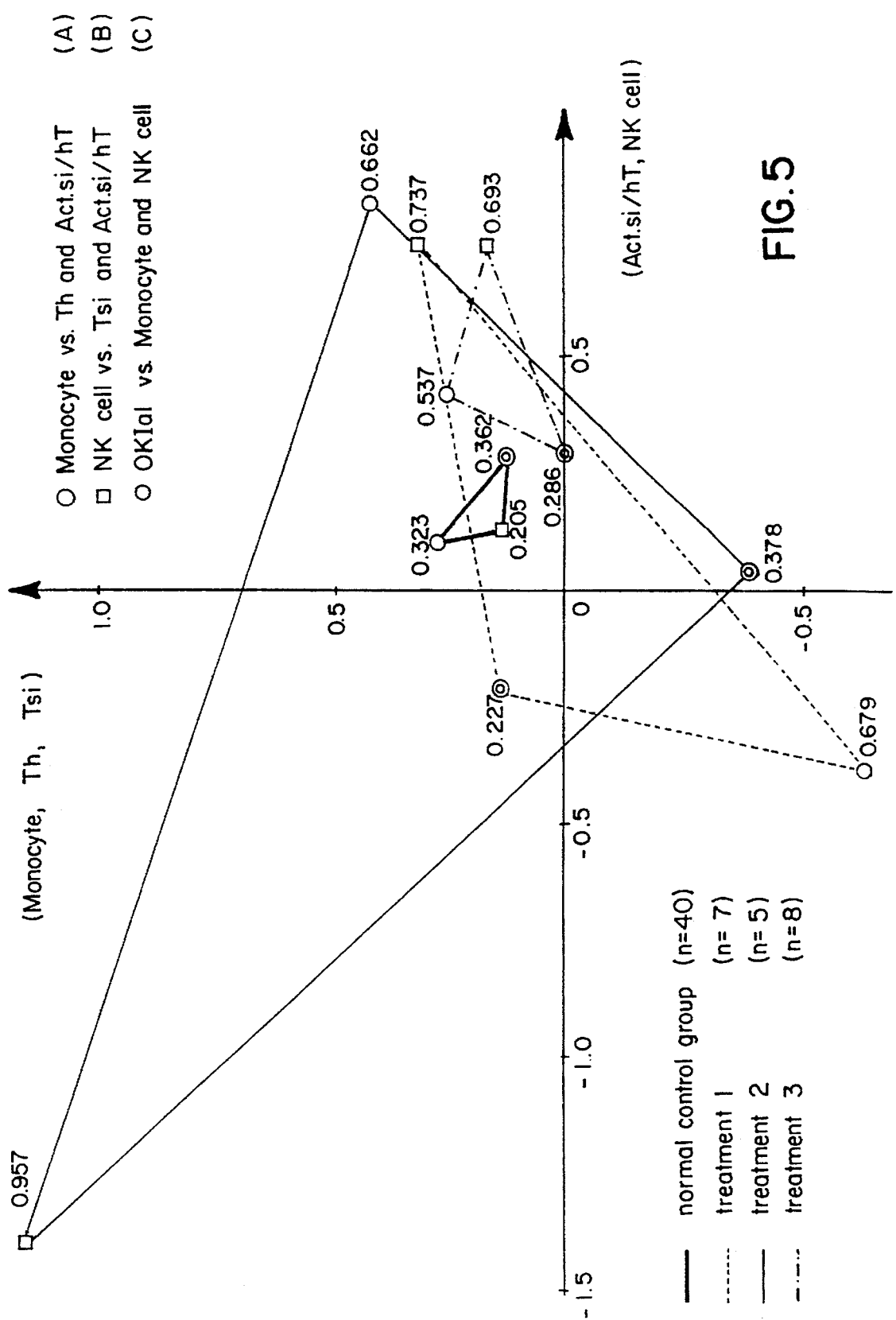
FIG. 5. The correlated graphs of immunologic three-factor sets obtained in accordance with Example 4
Figure 6B:
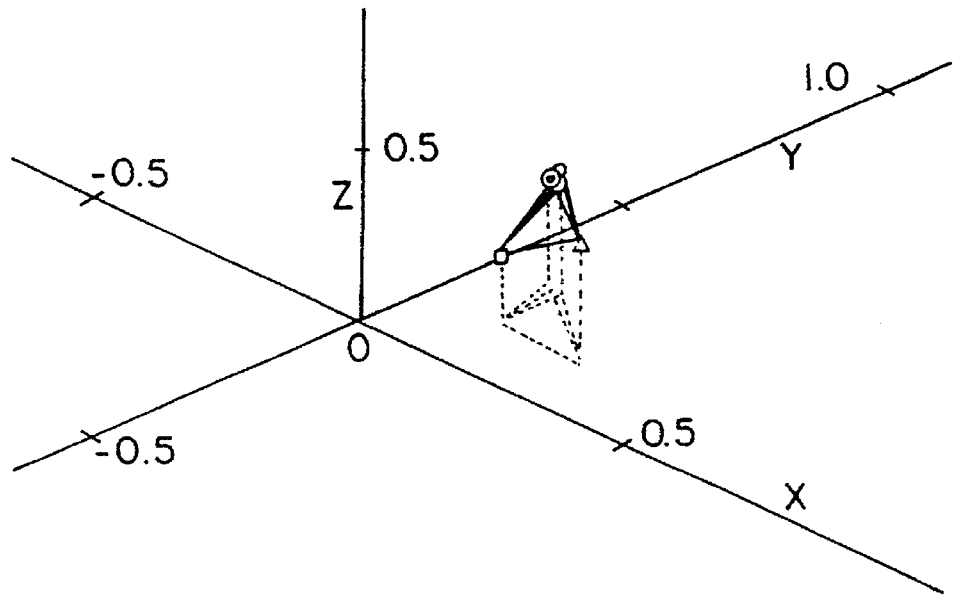
FIG. 6(A). The three-dimmensional representations of FIG. 3
FIGS. 6(B–D). The three-dimmensional graphs of the correlations of T and B cell immunologic three-factor sets obtained in Example 3(1)
Figure 6C:
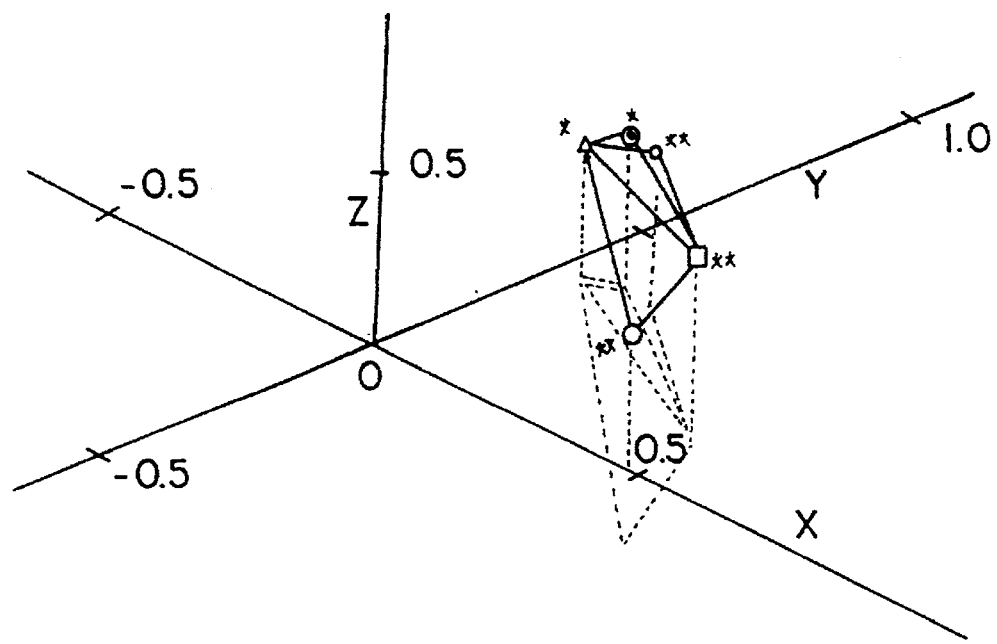
Figure 6D:
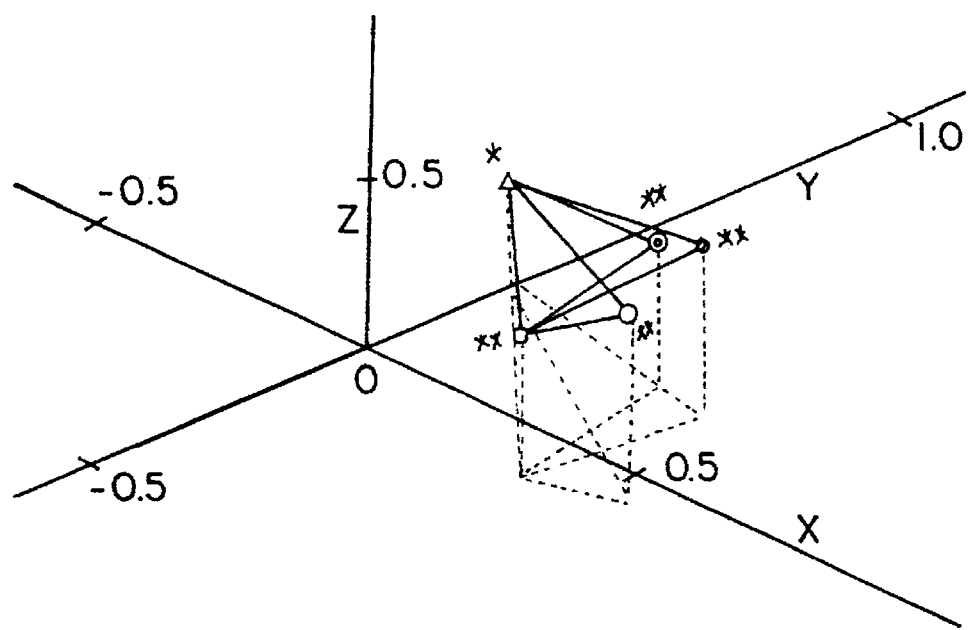
Figure 7:
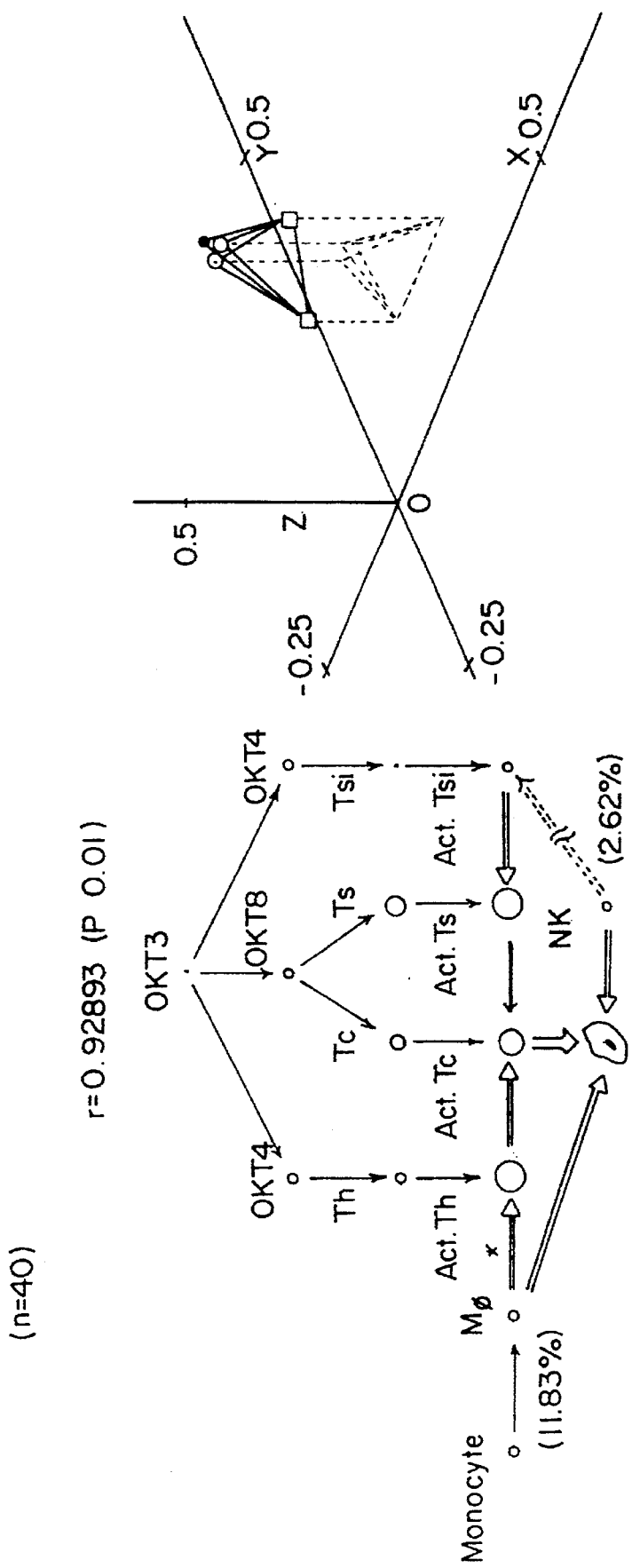
FIG. 7. T cell immunokinematogram, immunologic three-factor set and T and B cell immunologic three-factor sets on the 40 normal control group of Examples 1 and 2
Figure 8:
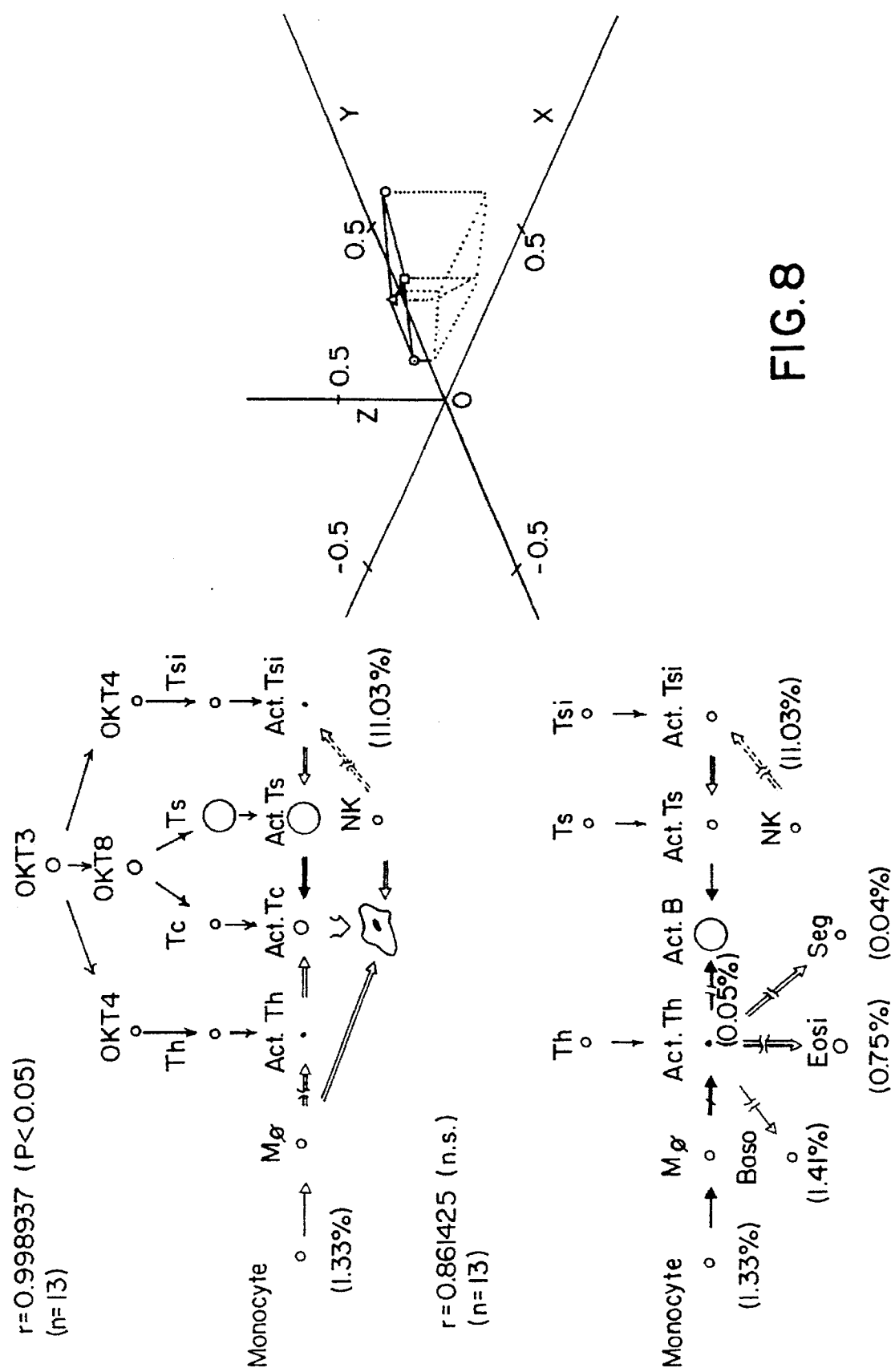
FIG. 8. T cell immunokinematogram, immunologic three-factor set and T and B cell immunologic three-factor sets on the 49 y.o. healthy male of Example 5
Figure 9:
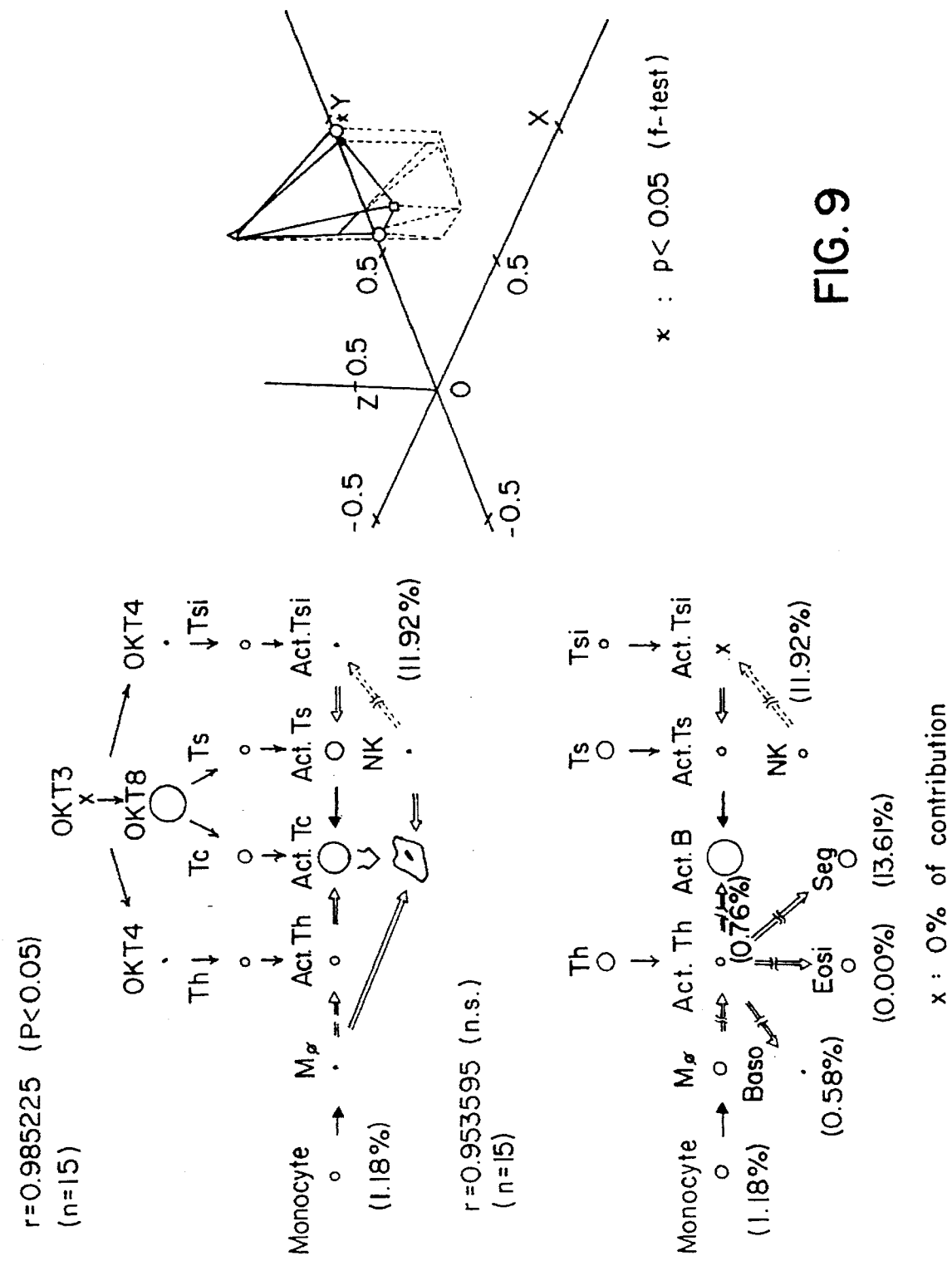
FIG. 9. T and B cell immunokinematograms, immunologic three-factor set and T and B cell immunologic three-factor sets on the three chronic rheumatoid arthritis patients of Example 6

I claim:

1. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) evaluating the immunokinetics of said patient; and iii) comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the subset of peripheral lymphocytes which are measured are the subset of monocytes, the subset of natural killer cells, the subset of OKIa1 positive lymphocytes, the subset of activated suppression inducer/helper T lymphocytes, the subset of activated suppressor/cytotoxic T lymphocytes, the subset of helper T lymphocytes and the subset of suppression inducer T lymphocytes, wherein the peripheral lymphocytes from said blood sample are labeled using fluorescently labeled monoclonal antibodies and the labeled cells are counted by flow cytometry, and wherein the immunokinetics of said patient are evaluated by:

a) determining standardized partial regression coefficients for the count of helper T lymphocytes and the count of activated suppression inducer/helper T lymphocytes by multiple regression analysis using the count of monocytes as a dependent variable and the count of helper T lymphocytes and the count of activated suppression inducer/helper T lymphocytes as independent variables to obtain correlations between the count of monocytes and the count of helper T lymphocytes and the count of activated suppression inducer/helper T lymphocytes;

b) determining standardized partial regression coefficients for the count of suppression inducer T lymphocytes and the count of activated suppression inducer/helper T lymphocytes by multiple regression analysis using the count of natural killer cells as a dependent variable and the count of suppression inducer T lymphocytes and the count of activated suppression inducer/helper T lymphocytes as independent variables to obtain correlations between the count of natural killer cells, the count of suppression inducer T lymphocytes, and the count of activated suppression inducer/helper T lymphocytes;

c) determining standardized partial regression coefficients for the count of natural killer cells and the count of monocytes by multiple regression analysis using the count of OKIa1 positive lymphocytes as a dependent variable and the count of natural killer cells and the count of monocytes as independent variables to obtain correlations between the count of OKIa1 positive lymphocytes, the count of natural killer cells and the count of monocytes;

d) determining standardized partial regression coefficient for the count of natural killer cells and the count of monocytes by multiple regression analysis using the sum of the counts of activated suppression inducer/helper T lymphocytes and the count of activated suppressor/cytotoxic T lymphocytes as a dependent variable and the count of natural killer cells and the count of monocytes as independent variables to obtain correlations between the count of activated T lymphocytes, the count of natural killer cells and the count of monocytes;

e) calculating an activated B lymphocyte count by subtracting the counts of activated suppression inducer/helper T lymphocytes and of activated suppressor/cytotoxic T lymphocytes from the count of OKIa1 positive lymphocytes;

f) determining standardized partial regression coefficients for the count of natural killer cells and the count of monocytes by multiple regression analysis using the count of activated B lymphocytes as a dependent variable and the count of natural killer cells and the count of monocytes as independent variables to obtain correlations between the count of activated B lymphocytes and the count of natural killer cells and the count of monocytes; and g) plotting all of the standardized partial regression coefficients on coordinates for assessment.

2. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) evaluating the immunokinetics of said patient; and iii) comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the subset of peripheral lymphocytes which are measured are the subsets of CD3, CD4 and CD8 positive lymphocytes, helper T lymphocytes, suppression inducer T lymphocytes, suppressor T lymphocytes, cytotoxic T lymphocytes, activated suppression inducer/helper T lymphocytes and activated suppressor/cytotoxic T lymphocytes, NK cells and monocytes, wherein the peripheral lymphocytes from said blood sample are labeled using fluorescently labeled monoclonal antibodies and the labeled cells are counted by flow cytometry, and wherein the immunokinetics of said patient are evaluated by:

a) performing multiple regression analysis using the count of activated suppressor/cytotoxic T lymphocytes as a dependent variable and the count of activated suppression inducer/helper T lymphocytes, the count of helper T lymphocytes, the count of suppression inducer T lymphocytes, the count of cytotoxic T lymphocytes, the count of suppressor T lymphocytes, the count of CD3 positive lymphocytes, the count of CD4 positive lymphocytes, the count of CD8 positive lymphocytes, the count of monocytes and the count of natural killer cells as independent variables;

b) determining contributions for each of the count of activated suppression inducer/helper T lymphocytes, the count of helper T lymphocytes, the count of suppression inducer T lymphocytes, the count of cytotoxic T lymphocytes, the count of suppressor T lymphocytes, the count of CD3 positive lymphocytes, the count of CD4 positive lymphocytes, the count of CD8 positive lymphocytes, the count of natural killer cells and the count of monocytes against the count of activated suppressor/cytotoxic T lymphocytes;

c) calculating contributions for the count of activated suppression inducer T lymphocytes and the count of activated helper T lymphocytes by allotting the contribution of the count of activated suppression inducer/helper T lymphocytes in proportion to the ratio of the contributions of the count of suppression inducer T lymphocytes and helper T lymphocytes;

d) calculating contributions for the count of activated suppressor T lymphocytes and the count of cytotoxic T lymphocytes by allotting the contribution of the count of activated suppressor/cytotoxic T lymphocytes obtained in step a) in proportion to the ratio between and contributions of the count of suppressor T lymphocytes and the count of cytotoxic T lymphocytes;

e) converting the contributions obtained in steps b) to d) into circular areas;

f) arranging the circular areas in accordance with mutual relationships among the count of activated helper, the count of activated suppression inducer T lymphocytes, the count of activated suppressor T lymphocytes and the count of activated cytotoxic T lymphocytes in order to draw integrated T cell immunokinematograms; and g) assessing the integrated T cell immunokinematograms.

3. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) evaluating the immunokinetics of said patient; and iii) comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the subset of peripheral lymphocytes which are measured are the subset of helper T lymphocytes, the subset of suppression inducer T lymphocytes, the subset of cytotoxic T lymphocytes, the subset of suppressor T lymphocytes, the subset of activated suppression inducer/helper T lymphocytes, the subset of activated suppressor/cytotoxic T lymphocytes, the subset OKIa1 positive lymphocytes, the subset of natural killer cells, the subset of monocytes, the subset of basophils, the subset of eosinophils and the subset of neutrophils, wherein the peripheral lymphocytes from said blood sample are labeled using fluorescently labeled monoclonal antibodies and the labeled cells are counted by flow cytometry, and wherein the immunokinetics of said patient are evaluated by:

a) calculating an activated B lymphocyte count by subtracting from the OKIa1 positive lymphocyte count, the sum of the activated suppression inducer/helper T lymphocyte and activated suppressor/cytotoxic T lymphocyte counts;

b) performing multiple regression analysis using the count of activated B lymphocytes as a dependent variable and the count of helper T lymphocytes, the count of suppression inducer T lymphocytes, the count of cytotoxic T lymphocytes, the count of suppressor T lymphocytes, the count of activated suppression inducer/helper T lymphocytes, the count of activated suppressor T lymphocytes, the count of cytotoxic T lymphocytes, the count of natural killer cells, the count of monocytes, the count of basophils, the count of eosinophils and the count of neutrophils as independent variables;

c) determining respective contributions of the count of helper T lymphocytes, the count of suppression inducer T lymphocytes, the count of cytotoxic T lymphocytes, the count of suppressor T lymphocytes, the count of activated suppressor/cytotoxic T lymphocytes, the count of natural killer cells, the count of monocytes, the count of basophils, the count of eosinophils and the count of neutrophils against the count of activated B lymphocytes;

d) calculating contributions of the count of activated helper T lymphocytes and the count of activated suppression inducer T lymphocytes by allotting the contribution of the count of activated suppression inducer/helper T lymphocytes in proportion to the ratio of the contributions of the count of helper T lymphocytes and the count of suppression inducer T lymphocytes;

e) allotting the contribution of the count of activated suppressor/cytotoxic T lymphocytes obtained in step b) in proportion to the ratio of the contributions of the count of suppressor T lymphocytes and the count of cytotoxic T lymphocytes in order to calculate contributions of the count of activated suppressor T lymphocytes and the count of activated cytotoxic T lymphocytes;

f) converting the respective contributions calculated in steps c), d) and e), except for the contributions of the count of cytotoxic T lymphocytes and the count of activated cytotoxic T lymphocytes, into circular areas;

g) arranging the circular areas in accordance with their mutual relationships in order to draw integrated B cell immunokinematograms; and h) assessing the integrated B cell immunokinematograms.

4. A method for evaluating a patient's response to chemotherapeutic or immunotherapeutic treatment comprising:

i) staining the cells in a blood sample from said patient with at least one monoclonal antibody;

ii) counting the number of monocytes, helper T lymphocytes and activated suppression inducer/helper T lymphocytes in said blood sample;

iii) performing multiple regression analysis using the count of the subset of monocytes as a dependent variable and the counts of the subset of helper T lymphocytes and the count of the subset of activated suppression inducer/helper T lymphocytes as independent variables;

iv) calculating a partial regression coefficient for the count of helper T lymphocytes and the count of activated suppression inducer/helper T lymphocytes and testing the significance of each partial regression coefficient;

v) calculating a multiple correlation coefficient from both partial regression coefficients and testing the significance of the multiple correlation coefficient;

vi) determining the contributions of the count of helper T lymphocytes and the count of activated suppression inducer/helper T lymphocytes;

vii) determining correlations between the count of monocytes and the count of helper T lymphocytes and the count of activated suppression inducer/helper T lymphocytes to assess said autologous tumor antigen recognition mechanism; and viii) comparing the correlations determined in step vii) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

5. A method for evaluating a patient's response to chemotherapeutic or immunotherapeutic treatment comprising:

i) staining the cells in a blood sample from said patient with at least one monoclonal antibody;

ii) counting the number of natural killer cells, suppression inducer T lymphocytes and helper T lymphocytes in said blood sample;

iii) performing multiple regression analysis using the count of the subset of natural killer cells as a dependent variable and the count of the subset of suppression inducer T lymphocytes and the count of the subset of activated suppression inducer/helper T lymphocytes as independent variables;

iv) calculating a partial regression coefficient for the count of suppression inducer T lymphocytes and the count of activated suppression inducer/helper T lymphocytes and testing the significance of each partial regressive coefficient;

v) calculating a multiple correlation coefficient and testing the significance thereof;

vi) determining the contributions of the count of suppression inducer T lymphocytes and the count of activated suppression inducer/helper T lymphocytes;

vii) determining correlations between the count of natural killer cells and the count of suppression inducer T lymphocytes and the count of activated suppression inducer/helper T lymphocytes to assess a suppressive function of natural killer cells in suppression of inducer T lymphocytes; and viii) comparing the correlations determined in step vii) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

6. A method for evaluating a patient's response to chemotherapeutic or immunotherapeutic treatment comprising:

i) staining the cells in a blood sample from said patient with at least one monoclonal antibody;

ii) counting the number of OKa1 positive lymphocytes, natural killer cells and monocytes in said blood sample;

iii) performing multiple regression analysis using the count of the subset OKIa1 positive lymphocytes as a dependent variable and using the count of the subset of natural killer cells and the count of the subset of monocytes as independent variables;

iv) calculating a respective partial regression coefficient for the count of natural killer cells and the count of monocytes and testing the significance of each partial regression coefficient;

v) calculating a multiple correlation coefficient from both partial regressive coefficients and testing the significance of the multiple correlation coefficient;

vi) determining the contributions of the count of natural killer cells and the count of monocytes;

vii) determining correlations between the count of OKIa1 positive lymphocytes and the count of natural killer cells and the count of monocytes to assess a function of natural killer cells and monocytes against OKIa1 positive lymphocytes; and viii) comparing the correlations determined in step vii) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

7. A method for evaluating a patient's response to chemotherapeutic or immunotherapeutic treatment comprising:

i) staining the cells in a blood sample from said patient with at least one monoclonal antibody;

ii) counting the number of monocytes, OKa1 positive lymphocytes, natural killer cells, activated suppression inducer/helper T lymphocytes and activated suppressor/cytotoxic T lymphocytes in said blood sample;

iii) calculating an activated B lymphocyte count by subtracting from the count of the subset of OKIa1 positive lymphocytes, the sum of the counts of the subset of activated suppression inducer/helper T lymphocytes and the subset of activated suppressor/cytotoxic T lymphocytes;

iv) performing multiple regression analysis using the count of activated B lymphocytes as a dependent variable and the count of the subset of natural killer cells and the count of the subset of monocytes as independent variables;

v) calculating a respective partial regression coefficient for the count of natural killer cells and the count of monocytes and testing the significance of each partial regression coefficient;

vi) calculating a multiple correlation coefficient from both partial regression coefficients and testing the significance of the multiple correlation coefficient;

vii) determining the contributions of the count of natural killer cells and the count of monocytes;

viii) determining correlations between the count of activated B lymphocytes and the count of natural killer cells and the count of monocytes to assess an effect of natural killer cells and monocytes on activated B lymphocytes; and ix) comparing the correlations determined in step viii) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

8. A method for evaluating a patient's response to chemotherapeutic or immunotherapeutic treatment comprising:

i) treating a blood sample of said patient with an anticoagulant and counting the number of monocytes, helper T lymphocytes and activated suppression inducer/helper T lymphocytes in said blood sample;

ii) performing multiple regression analysis using the count of the subset of monocytes as a dependent variable and the counts of the subset of helper T lymphocytes and the count of the subset of activated suppression inducer/helper T lymphocytes as independent variables;

iii) calculating a partial regression coefficient for the count of helper T lymphocytes and the count of activated suppression inducer/helper T lymphocytes and testing the significance of each partial regression coefficient;

iv) calculating a multiple correlation coefficient from both partial regression coefficients and testing the significance of the multiple correlation coefficient;

v) determining the contributions of the count of helper T lymphocytes and the count of activated suppression inducer/helper T lymphocytes;

vi) determining correlations between the count of monocytes and the count of helper T lymphocytes and the count of activated suppression inducer/helper T lymphocytes to assess said autologous tumor antigen recognition mechanism; and vii) comparing the correlations determined in step vi) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

9. A method for evaluating a patient's response to chemotherapeutic or immunotherapeutic treatment comprising:

i) treating a blood sample of said patient with an anticoagulant and counting the number of natural killer cells, suppression inducer T lymphocytes and helper T lymphocytes in said blood sample;

ii) performing multiple regression analysis using the count of the subset of natural killer cells as a dependent variable and the count of the subset of suppression inducer T lymphocytes and the count of the subset of activated suppression inducer/helper T lymphocytes as independent variables;

iii) calculating a partial regression coefficient for the count of suppression inducer T lymphocytes and the count of activated suppression inducer/helper T lymphocytes and testing the significance of each partial regressive coefficient;

iv) calculating a multiple correlation coefficient and testing the significance thereof;

v) determining the contributions of the count of suppression inducer T lymphocytes and the count of activated suppression inducer/helper T lymphocytes;

vi) determining correlations between the count of natural killer cells and the count of suppression inducer T lymphocytes and the count of activated suppression inducer/helper T lymphocytes to assess a suppressive function of natural killer cells in suppression of inducer T lymphocytes; and vii) comparing the correlations determined in step vi) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

10. A method for evaluating a patient's response to chemotherapeutic or immunotherapeutic treatment comprising:

i) treating a blood sample of said patient with an anticoagulant and counting the number of OKa1 positive lymphocytes, natural killer cells and monocytes in said blood sample;

ii) performing multiple regression analysis using the count of the subset OKIa1 positive lymphocytes as a dependent variable and using the count of the subset of natural killer cells and the count of the subset of monocytes as independent variables;

iii) calculating a respective partial regression coefficient for the count of natural killer cells and the count of monocytes and testing the significance of each partial regression coefficient;

iv) calculating a multiple correlation coefficient from both partial regressive coefficients and testing the significance of the multiple correlation coefficient;

v) determining the contributions of the count of natural killer cells and the count of monocytes;

vi) determining correlations between the count of OKIa1 positive lymphocytes and the count of natural killer cells and the count of monocytes to assess a function of natural killer cells and monocytes against OKIa1 positive lymphocytes; and vii) comparing the correlations determined in step vi) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

11. A method for evaluating a patient's response to chemotherapeutic or immunotherapeutic treatment comprising:

i) treating a blood sample of said patient with an anticoagulant and counting the number of monocytes, OKa1 positive lymphocytes, natural killer cells, activated suppression inducer/helper T lymphocytes and activated suppressor/cytotoxic T lymphocytes in said blood sample;

ii) calculating an activated B lymphocyte count by subtracting from the count of the subset of OKIa1 positive lymphocytes, the sum of the counts of the subset of activated suppression inducer/helper T lymphocytes and the subset of activated suppressor/cytotoxic T lymphocytes;

iii) performing multiple regression analysis using the count of activated B lymphocytes as a dependent variable and the count of the subset of natural killer cells and the count of the subset of monocytes as independent variables;

iv) calculating a respective partial regression coefficient for the count of natural killer cells and the count of monocytes and testing the significance of each partial regression coefficient;

v) calculating a multiple correlation coefficient from both partial regression coefficients and testing the significance of the multiple correlation coefficient;

vi) determining the contributions of the count of natural killer cells and the count of monocytes;

vii) determining correlations between the count of activated B lymphocytes and the count of natural killer cells and the count of monocytes to assess an effect of natural killer cells and monocytes on activated B lymphocytes; and viii) comparing the correlations determined in step vii) with the similar mean values and error estimates of the same correlations determined from a population of individuals who respond favorably to said chemotherapeutic or immunotherapeutic treatment and a population of individuals who do not respond to said chemotherapeutic or immunotherapeutic treatment, to make an evaluation of said patient's response to said chemotherapeutic or immunotherapeutic treatment.

12. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) staining the peripheral lymphocytes with at least one monoclonal antibody;

iii) evaluating the immunokinetics of said patient; and iv) comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the response of said patient to be evaluated is establishment of an autologous tumor antigen recognition mechanism, and wherein the subsets of peripheral lymphocytes to be counted are the subset of monocytes, the subset of helper T lymphocytes and the subset of activated suppression inducer/helper T lymphocytes; wherein the evaluation of the immunokinetics of said patient is performed by:

a) performing multiple regression analysis using the count of the subset of monocytes as a dependent variable and the counts of the subset of helper T lymphocytes and the count of the subset of activated suppression inducer/helper T lymphocytes as independent variables;

b) calculating a partial regression coefficient for the count of helper T lymphocytes and the count of activated suppression inducer/helper T lymphocytes and testing the significance of each partial regression coefficient;

c) calculating a multiple correlation coefficient from both partial regression coefficients and testing the significance of the multiple correlation coefficient;

d) determining the contributions of the count of helper T lymphocytes and the count of activated suppression inducer/helper T lymphocytes; and e) determining correlations between the count of monocytes and the count of helper T lymphocytes and the count of activated suppression inducer/helper T lymphocytes to assess said autologous tumor antigen recognition mechanism.

13. The method of claim 12, wherein said chemotherapeutic or immunotherapeutic treatment comprises administering to said patient a composition selected from the group consisting of human lymphoblastoid interferon, UFT, doxifluridine, vinblastine, adriamycin, OK-432, γ-interferon and $N^2$-(N-acetylmuramyl-L-alanyl-D-isoglutamyl)-$N^6$-stearoyl-L-lysine.

14. The method of claim 12, wherein said at least one monoclonal antibody for staining the lymphocytes is fluorescently-labeled and the stained cells are counted by fluorescence-activated cell sorting.

15. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) staining the peripheral lymphocytes with at least one monoclonal antibody;

iii) evaluating the immunokinetics of said patient; and iv) comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the response of said patient to be evaluated is function of natural killer cells, wherein the subsets of peripheral lymphocytes to be counted are the subset of natural killer cells, the subset of suppression inducer T lymphocytes and the subset of activated suppression inducer/helper T lymphocytes; wherein evaluation of the immunokinetics of said patient is performed by:

a) performing multiple regression analysis using the count of the subset of natural killer cells as a dependent variable and the count of the subset of suppression inducer T lymphocytes and the count of the subset of activated suppression inducer/helper T lymphocytes as independent variables;

b) calculating a partial regression coefficient for the count of suppression inducer T lymphocytes and the count of activated suppression inducer/helper T lymphocytes and testing the significance of each partial regressive coefficient;

c) calculating a multiple correlation coefficient and testing the significance thereof;

d) determining the contributions of the count of suppression inducer T lymphocytes and the count of activated suppression inducer/helper T lymphocytes; and e) determining correlations between the count of natural killer cells and the count of suppression inducer T lymphocytes and the count of activated suppression inducer/helper T lymphocytes to assess a suppressive function of natural killer cells in suppression of inducer T lymphocytes.

16. The method of claim 15, wherein said at least one monoclonal antibody for staining the lymphocytes is fluorescently-labeled and the stained cells are counted by fluorescence-activated cell sorting.

17. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) staining the peripheral lymphocytes with at least one monoclonal antibody;

iii) evaluating the immunokinetics of said patient; and iv comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the response of said patient to be evaluated is cooperative function among activated lymphocytes, monocytes and natural killer cells, wherein the subsets of peripheral lymphocytes to be counted are the subset of OKIa1 positive lymphocytes, the subset of natural killer cells and the subset of monocytes; wherein evaluation of the immunokinetics of said patient is performed by:

a) performing multiple regression analysis using the count of the subset OKIa1 positive lymphocytes as a dependent variable and using the count of the subset of natural killer cells and the count of the subset of monocytes as independent variables;

b) calculating a respective partial regression coefficient for the count of natural killer cells and the count of monocytes and testing the significance of each partial regression coefficient;

c) calculating a multiple correlation coefficient from both partial regressive coefficients and testing the significance of the multiple correlation coefficient;

d) determining the contributions of the count of natural killer cells and the count of monocytes; and e) determining correlations between the count of OKIa1 positive lymphocytes and the count of natural killer cells and the count of monocytes to assess a function of natural killer cells and monocytes against OKIa1 positive lymphocytes.

18. The method of claim 17, wherein said at least one monoclonal antibody for staining the lymphocytes is fluorescently-labeled and the stained cells are counted by fluorescence-activated cell sorting.

19. A method for providing evaluation and prognosis of a patient's response to chemotherapeutic or immunotherapeutic treatment of a disease, which comprises:

i) drawing a blood sample from said patient and measuring the counts of subsets of the peripheral lymphocytes of said patient;

ii) staining the peripheral lymphocytes with at least one monoclonal antibody;

iii evaluating the immunokinetics of said patient; and iv comparing the immunokinetics of said patient to a database of mean values and error estimates of immunokinetic parameters obtained from a database of said values from a population of normal individuals, a population of individuals who respond favorably to said chemotherapeutic or immunotherapeutic treatment and a population of individuals who do not respond to said chemotherapeutic or immunotherapeutic treatment, to make an evaluation and prognosis of said patient's response to said chemotherapeutic or immunotherapeutic treatment, wherein the response of said patient to be evaluated is cooperative function among activated B lymphocytes, monocytes and natural killer cells, wherein said subsets of peripheral lymphocytes to measured are the subset of monocytes, the subset of natural killer cells, the subset of OKIa1 positive lymphocytes, the subset of activated suppression inducer/helper T lymphocytes and the subset of activated suppressor/cytotoxic T lymphocytes; wherein evaluation of the immunokinetics of said patient is performed by:

a) calculating an activated B lymphocyte count by subtracting from the count of the subset of OKIa1 positive lymphocytes, the sum of the counts of the subset of activated suppression inducer/helper T lymphocytes and the subset of activated suppressor/cytotoxic T lymphocytes;

b) performing multiple regression analysis using the count of activated B lymphocytes as a dependent variable and the count of the subset of natural killer cells and the count of the subset of monocytes as independent variables;

c) calculating a respective partial regression coefficient for the count of natural killer cells and the count of monocytes and testing the significance of each partial regression coefficient;

d) calculating a multiple correlation coefficient from both partial regression coefficients and testing the significance of the multiple correlation coefficient;

e) determining the contributions of the count of natural killer cells and the count of monocytes; and f) determining correlations between the count of activated B lymphocytes and the count of natural killer cells and the count of monocytes to assess an effect of natural killer cells and monocytes on activated B lymphocytes.

20. The method of claim 19, wherein said at least one monoclonal antibody for staining the lymphocytes is fluorescently-labeled and the stained cells are counted by fluorescence-activated cell sorting.

* * * * *